US009533044B2

(12) United States Patent
Maloney

(10) Patent No.: US 9,533,044 B2
(45) Date of Patent: Jan. 3, 2017

(54) METHODS OF TREATING INFLAMMATORY DISORDERS USING HIGH CONCENTRATION NATALIZUMAB COMPOSITIONS

(75) Inventor: Kevin Maloney, Nashua, NH (US)

(73) Assignee: BIOGEN MA INC., Cambridge, MA (US)

( * ) Notice: Subject to any disclaimer, the term of this patent is extended or adjusted under 35 U.S.C. 154(b) by 620 days.

(21) Appl. No.: 13/530,879

(22) Filed: Jun. 22, 2012

(65) Prior Publication Data
US 2013/0017193 A1 Jan. 17, 2013

Related U.S. Application Data

(63) Continuation of application No. 13/359,959, filed on Jan. 27, 2012, now abandoned, which is a continuation of application No. 12/139,362, filed on Jun. 13, 2008, now abandoned.

(60) Provisional application No. 60/944,076, filed on Jun. 14, 2007.

(51) Int. Cl.
A61K 39/395 (2006.01)
C07K 16/28 (2006.01)

(52) U.S. Cl.
CPC ..... A61K 39/39591 (2013.01); C07K 16/2839 (2013.01); C07K 2317/24 (2013.01)

(58) Field of Classification Search
None
See application file for complete search history.

(56) References Cited

U.S. PATENT DOCUMENTS

| 3,773,919 | A | 11/1973 | Boswell et al. |
| 4,399,216 | A | 8/1983 | Axel et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,596,556 | A | 6/1986 | Morrow et al. |
| 4,634,665 | A | 1/1987 | Axel et al. |
| 4,767,628 | A | 8/1988 | Hutchinson |
| 4,790,824 | A | 12/1988 | Morrow et al. |
| 4,941,880 | A | 7/1990 | Burns |
| 5,064,413 | A | 11/1991 | McKinnon et al. |
| 5,179,017 | A | 1/1993 | Axel et al. |
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,530,101 | A | 6/1996 | Queen et al. |
| 5,585,089 | A | 12/1996 | Queen et al. |
| 5,693,761 | A | 12/1997 | Queen et al. |
| 5,693,762 | A | 12/1997 | Queen et al. |
| 5,789,650 | A | 8/1998 | Lonberg et al. |
| 5,798,230 | A | 8/1998 | Bornkamm et al. |
| 5,840,299 | A | 11/1998 | Bendig et al. |
| 5,849,992 | A | 12/1998 | Meade et al. |
| 5,888,507 | A | 3/1999 | Burkly |
| 6,258,562 | B1 | 7/2001 | Salfeld et al. |
| 6,407,213 | B1 | 6/2002 | Carter et al. |
| 6,602,503 | B1 | 8/2003 | Lobb et al. |
| 6,914,128 | B1 | 7/2005 | Salfeld et al. |
| 8,349,321 | B2 | 1/2013 | Burke et al. |
| 8,815,236 | B2 | 8/2014 | Burke et al. |
| 2001/0014326 | A1 | 8/2001 | Andya et al. |
| 2003/0070185 | A1 | 4/2003 | Jakobovits et al. |
| 2003/0232333 | A1 | 12/2003 | Ladner et al. |
| 2005/0053598 | A1 | 3/2005 | Burke et al. |
| 2009/0202527 | A1* | 8/2009 | Panzara et al. ............ 424/133.1 |
| 2015/0030590 | A1 | 1/2015 | Panzara |

FOREIGN PATENT DOCUMENTS

| EP | 0234900 A2 | 9/1987 |
| WO | 9007861 A1 | 7/1990 |
| WO | 9415587 A2 | 7/1994 |
| WO | 9519790 A1 | 7/1995 |
| WO | 9634096 A1 | 10/1996 |
| WO | 0155112 A1 | 8/2001 |
| WO | 2004071439 A2 | 8/2004 |
| WO | 2008021954 A2 | 2/2008 |

OTHER PUBLICATIONS

Rudikoff et al., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., Embo J., 14: 2784-2794 (1995).*
Arthritis & Rheumatism (1996) vol. 39, No. 9 (supplement), S284.
Baumgartner et al, (1996) "Double Blind, Placebo Controlled Trail of Tumor Necrosis Factor Receptor Fusion Protein (TNFR:Fc) In Active Rheumatoid Arthritis" J. Invest. Med., 44: 235A.
Bird et al. (1988) "Single-Chain Antigen-Binding Proteins" Science 242:423-426.
Boerner et al. (1991) "Production of Antigen-Specific Human Monoclonal Antibodies From In Vitro-Primed Human Splenocytes" J. Immunol. 147:86-95.
Burton and Woof (1992) "Human Antibody Effector Function" Adv. Immunol. 51:1-84.
Chothia et al. (1987) "Canonical Structures for the Hypervariable Regions of Immunoglobulins" J. Mol. Biol. D 196:901-917.
Daugherty Ann L. et al.,(2006) Formulation and delivery issues for monoclonal antibody therapeutics, Advanced Drug D Delivery Reviews, 58: 686-706.
Green et al. (1994) "Antigen-specific human monoclonal antibodies from mice engineered with human Ig heavy and light chain YACs" Nature Genetics 7:13-21.
Harris et al., (2004) "Commercial manufacturing scale formulation and analytical characterization of therapeutic recombinant antibodies," Drug Development Research, New York, NY, 61 :137-154.
Hemler et al. (1987) "Characterization of the Cell Surface Heterodimer VLA-4 and Related Peptides" J. Biol. Chem. 262:11478-11485.

(Continued)

Primary Examiner — Phillip Gambel
(74) Attorney, Agent, or Firm — Lando & Anastasi, LLP

(57) ABSTRACT

Formulations of VLA-4 binding antibody are described.

44 Claims, 8 Drawing Sheets

(56) References Cited

OTHER PUBLICATIONS

Hoogenboom et al. (1998) "Antibody phage display technology and its applications" Immunotechnology 4: 1-20.

Hoogenboom et al. (2000) "Natural and designer binding sites made by phage display technology" Immunol. Today 21 :371-8.

Huang and Stollar (1991) "Construction of representative immunoglobulin variable region cDNA libraries from human peripheral blood lymphocytes without in vitro stimulation" J. Immunol. Methods 141 :227-236.

Huston et al., (1988) "Protein engineering of antibody binding sites: Recovery of specific activity in an anti-digoxin single-chain Fv analogue produced in *Escherichia coli*," Proc. Natl. Acad. Sci. USA 85:5879-5883.

International Preliminary Report on Patentability and Written Opinion from application PCT/US2008/066928 dated Dec. 30, 2009.

Issekutz and Wykretowicz (1991) "Effect of a New Monoclonal Antibody, TA-2, That Inhibits Lymphocyte Adherence to Cytokine Stimulated Endothelium in the Rat," J. Immunol. 147:109-116.

Jefferis et al. (1998) "IgG-Fc-mediated effector functions: molecular definition of interaction sites for effector ligands and the role of glycosylation," Immunol. Rev. 163:59-76.

Kaufman and Sharp (1982) "Amplification and Expression of Sequences Cotransfected with a Modular Dihydrofolate Reductase Complementary DNA Gene," J. Mol. Biol. 159:601-621.

Kurtzke (1983) "Rating neurologic impairment in multiple sclerosis: An expanded disability status scale (EDSS)," Neurology, 33:1444.

Kurtzke (1994) "Clinicial Definition for Multiple Sclerosis Treatment Trials," Ann. Neurol. 36:S573-S79.

McDonald et al. (1994) "Are Magnetic Resonance Findings Predictive of Clinical Outcome in Therapeutic Trials in Multiple Sclerosis? The Dilemma of Interferon-B," Ann. Neurol. 36:14.

McDonald et al.,( 2001), Recommended diagnostic criteria for multiple sclerosis: guidelines from the International Panel on the Diagnosis of Multiple Sclerosis, Ann Neurol. 50:121-127.

O'Dell et al, (1994) "Triple DMARD Therapy for Rheumatoid Arthritis" Arthritis & Rheumatism, 37: S295.

Paty et al. (1993) "Interferon beta-1 b is effective in relapsing-remitting multiple sclerosis," Neurology 43:665.

Persson et al. (1991) "Generation of diverse high-affinity human monoclonal antibodies by repertoire cloning," Proc. Natl. Acad. Sci USA 88:2432-2436.

Poser et al. (1983) "New Diagnostic Criteria for Multiple Sclerosis: Guidelines for Research Protocols," Ann. Neurol. 13:227.

Powers et al. (2001) "Expression of single-chain Fv-Fc fusions in Pichia pastoris," J. Immunol. Methods 251: 123-35.

Pulido et al. (1991) "Functional Evidence for Three Distinct and Independently Inhibitable Adhesion Activities Mediated by the Human Integrin VLA-4," J. Biol. Chem. 266:10241-10245.

Riechmann et al. (1988) "Reshaping human antibodies for therapy," Nature 332:323-327.

Rudikoff et al., (1982) "Single amino acid substitution altering antigen-binding specificity", Proc. Nat. Acad. Sci., 79: D 1979-1983.

Sanchez-Madrid et al. (1986) "VLA-3: A novel polypeptide association within the VLA molecular complex: cell distribution and biochemical characterization," Eur. J. Immunol. 16:1343-1349.

Shire et al.,(2004) "Challenges in the development of high protein concentration formulations," Journal of Pharmaceutical Sciences, 93: 1390-1402.

Sipe et al. (1984) "A neurologic rating scale (NRS) for use in multiple sclerosis," Neurology 34: 1368.

Sobel et al. (1984) "The Immunopathology of Experimental Allergic Encephalomyelitis," J. Immunol. 132: 2393-2401.

Tempest et al. (1991) "Reshaping a Human Monoclonal Antibody to Inhibit Human Respiratory Syncytial Virus Infection In Vivo," Biotechnology 9:266-271.

Traugott (1989) "Detailed Analysis of Early Immunopathologic Events during Lesion Formation in Acute Experimental Autoimmune Encephalomyelitis," Cellular Immunol. 119: 114-129.

Tuohy et al. (1988) "A Synthetic Peptide From Myelin Proteolipid Protein Induces Experimental Allergic Encephalomyelitis," J. Immunol. 141 :1126-1130.

Urlaub et al. (1980) "Isolation of Chinese hamster cell mutants deficient in dihydrofolate reductase activity," Proc. Natl. Acad. Sci USA 77:4216-4220.

Vaughan et ai, (1996) "Human Antibodies with Sub-nanomolar Affinities Isolated from a Large Non-immunized Phage Display Library," Nature Biotechnology 14:309-314.

Verhoeyen et al. (1988) "Reshaping Human Antibodies: Grafting an Antilysozyme Activity," Science 239:1534-1536.

Vollmer et al., (2004) "An open-label safety and drug interaction study of natalizumab (Antegren™) in combination with interferon-beta (Avonex®) in patients with multiple sclerosis", Multiple Sclerosis, 1 0:511-520.

Wakankar et al., (2007) The effect of cosolutes on the isomerization of aspartic acid residues and conformational D stability in a monoclonal antibody, Journal of Pharmaceutical Science, 96:1708-1718.

Wang et al., (2007) "Antibody Structure, Instability, and Formulation", J. Pharma. Sci., 9:1-26.

Ward et al. (1989) Binding activities of a repertoire of single immunoglobulin variable domains secreted from *Escherichia colil*: Nature 341 :544-546.

Polman, et al., "A Randomized, Placebo-Controlled Trial of Natalizumab for Relapsing Multiple Sclerosis" New England Journal of Medicine, vol. 354, No. 9., p. 899-910, Mar. 2006.

Sandborn, et al., Natalizumab Induction and Maintenance Therapy for Crohn's Disease, N Engl J Med 2005; vol. 353, pp. 1912-1925.

International Search Report for International Application No. PCTUS2008066928 dated Oct. 12, 2008.

Aversano, Thomas et al., A Chimeric IgG4 Monoclonal Antibody Directed Against CD18 Reduces Infarct Size in a Primate Model of Myocardial Ischemia and Reperfusion, 25(3) JACC 781 (1995).

Bell, Jenny and Colaneri, Jean, Zenapax: Transplant's First Humanized Monoclonal Antibody, 25(4) ANNA Journal 429 (1998).

Cellular and Molecular Immunology, (Abul K. Abbas et al. W.B. Saunders Co., 3rd edition, 1997).

Chemical Stability of Pharmaceuticals: A Handbook for Pharmacists, 8-32 (Kenneth A. Connors, et al., eds., 1986).

Cleland et al., 10, Critical Reviews in Therapeutic Drug Carrier Systems, 307-377 (2000).

Cummins, Larry M. et al., Preparation and Characterization of an Intravenous Solution of IgG From Human Immunodeficiency Virus-Seropositive Donors, 77 Blood 1111 (1991).

Fundamental Immunology, 47-57 (William E. Paul ed., Lippincott-Raven, 4th edition, 1999).

Gordon, Fiona H. et al., A Randomized Placebo-Controlled Trial of a Humanized Monoclonal Antibody to ?4 Integrin in Active Crohn's Disease, 121 Gastroenterology 268 (2001).

Martin, Alfred et al., Physical Pharmacy, 222-39, 391-92 (1983).

Mikulandra, F., The Effect of High Birth Weight (4000 g or More) on the Weight and Height of Adult Men and Women, 24 Coll. Antropol. 133-136 (2000).

Naropin®, in Physicians' Desk Reference 609 (54th ed. 2000).

Orthoclone®, in Physicians' Desk Reference 1837 (50th ed. 1996).

Petition for inter partes review of 8,349,321 dated Apr. 18, 2016.

Petition for inter partes review of 8,815,236 dated Apr. 18, 2016.

Petition for inter partes review of 8,900,577 dated Apr. 18, 2016.

Pharmaceutical Formulation Development of Peptides and Proteins, 146-47, 150-52, 160-65, 171 (Sven Frokjaer and Lars Hovgaard eds., Taylor & Francis Ltd. 2000).

Protein Formulation and Delivery Preface, 139-158 (Eugene J. McNally ed., Marcel Dekker, Inc. 2000).

Remington: The Science and Practice of Pharmacy, 250-51, 819, 1265 (2000).

Sands, Bruce E. et al., Infliximab in the Treatment of Severe, Steroid-Refractory Ulcerative Colitis: A Pilot Study, 7 Inflammatory Bowel Diseases 83 (2001).

Sheremata, W. A. et al., A Safety and Pharmacokinetic Study of Intravenous Natalizumab in Patients with MS, 52 Neurology 1072 (1999).

Sorbera, L.A. et al., Natalizumab Treatment of IBD Treatment of Multiple Sclerosis, 25 Drugs of the Future 917 (2000).

(56) References Cited

OTHER PUBLICATIONS

Subramanian, Malathy et al., Effect of Histidine Oxidation on the Loss of Potency of a Humanized Monoclonal Antibody, AAPS Pharmsci, S-29 (Oct 2001).
van Oosten, B.W. et al., Increased MRI Activity and Immune Activation in Two Multiple Sclerosis Patients Treated with the Monoclonal Anti-Tumor Necrosis Factor Antibody cA2, 47 Neurology 1531 (1996).
Wang et al., 185, International Journal of Pharmaceutics, 129-188 (1999).
White, John Stephen et al., Proteins, Peptides and Amino Acids: SourceBook, 108-112 (2002).
Xylocaine®, in Physicians' Desk Reference 638 (54th ed. 2000).
Zenapax®, in Physicians' Desk Reference 2696 (54th ed. 2000).

* cited by examiner

SEQUENCE LISTING

```
<160> NUMBER OF SEQ ID NOS: 2

<210> SEQ ID NO 1
<211> LENGTH: 213
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asp Ile Asn Lys Tyr
            20                  25                  30

Met Ala Trp Tyr Gln Gln Thr Pro Gly Lys Ala Pro Arg Leu Leu Ile
        35                  40                  45
```

His Tyr Thr Ser Ala Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 2
<211> LENGTH: 450
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Arg Leu Glu Trp Met
        35                  40                  45

Gly Arg Ile Asp Pro Ala Asn Gly Tyr Thr Lys Tyr Asp Pro Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Asn Tyr Gly Val Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

```
Thr Val Pro Ser Ser Ser Leu Gly Thr Lys Thr Tyr Thr Cys Asn Val
    195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
450
```

METHODS OF TREATING INFLAMMATORY DISORDERS USING HIGH CONCENTRATION NATALIZUMAB COMPOSITIONS

CROSS-REFERENCE TO RELATED APPLICATIONS

This application is a continuation of U.S. application Ser. No. 13/359,959, filed Jan. 27, 2012, now abandoned, which is a continuation of U.S. application Ser. No. 12/139,362, filed Jun. 13, 2008, now abandoned, which claims priority to U.S. Application Ser. No. 60/944,076, filed on Jun. 14, 2007. The entire contents of each of the foregoing applications are incorporated herein by reference.

BACKGROUND

Multiple sclerosis (MS) is one of the most common diseases of the central nervous system. Today over 2,500,000 people around the world have MS.

SUMMARY

The invention is based, in part, on the development of formulations containing high concentrations of VLA-4 binding antibody. Some embodiments are suitable for delivery to a subject, such as a human, e.g., a human patient, by subcutaneous (SC) or intramuscular (IM) delivery. The formulations are also suitable for intravenous (IV) administration, e.g., when diluted into an acceptable infusion matrix (such as normal saline). The VLA-4 binding antibody can be natalizumab, for example, and the antibody concentration ranges from about 120 mg/mL to about 190 mg/mL. The formulations provide a therapeutic effect for an inflammatory, immune, or autoimmune disorder. For example, the formulation can provide a therapeutic effect for a central nervous system (CNS) inflammatory disorder, such as multiple sclerosis (MS).

In one aspect, the invention features an aqueous pharmaceutical composition, such as a stable aqueous pharmaceutical composition, containing a VLA-4 binding antibody at a concentration of about 120 to about 190 mg/mL (e.g., at a concentration of about 135 mg/mL, about 140 mg/mL, about 150 mg/mL, about 160 mg/mL, or about 165 mg/mL), and a phosphate buffer having about pH 5.5 to about pH 6.5. In some embodiments, the VLA-4 antibody concentration is from about 130 mg/mL to about 180 mg/mL or about 140 mg/mL to about 160 mg/mL. In one embodiment, the VLA-4 antibody concentration is greater than about 150 mg/mL, e.g., it is in a range of greater than about 150 mg/mL to about 190 mg/mL. In one embodiment, the VLA-4 antibody concentration is about 150 mg/mL.

In one embodiment, the VLA-4 binding antibody is a humanized monoclonal antibody, such as natalizumab. In another embodiment, the VLA-4 binding antibody is a variant of natalizumab. For example, in some embodiments, the light chain variable region of the antibody has an amino acid sequence that differs by one or more amino acid residues, but not more than 2, 3, 4, 5, or 6 amino acid residues of the light chain variable region of natalizumab, and/or the heavy chain variable region has an amino acid sequence that differs by one or more amino acid residues, but not more than 2, 3, 4, 5, or 6 amino acid residues of the heavy chain variable region of natalizumab. In some embodiments, some or all differences are conservative changes.

In another embodiment, the VLA-4 binding antibody has one or both of a light chain variable region having the amino acid sequence of SEQ ID NO:7 in U.S. Pat. No. 5,840,299, which is incorporate by reference herein, and a heavy chain variable region having the amino acid sequence of SEQ ID NO:11 in U.S. Pat. No. 5,840,299. In other embodiments, the VLA-4 antibody is a variant of one of these antibodies. For example, in some embodiments, the light chain variable region has an amino acid sequence that differs by one or more amino acid residues, but not more than 2, 3, 4, 5, or 6 amino acid residues from the sequence in SEQ ID NO:7 in U.S. Pat. No. 5,840,299, and/or the heavy chain variable region has an amino acid sequence that differs by one or more amino acid residues, but not more than 2, 3, 4, 5, or 6 amino acid residues as defined by SEQ ID NO:11 in U.S. Pat. No. 5,840,299.

In yet another embodiment, the VLA-4 binding antibody has one or both of a light chain amino acid sequence of SEQ ID NO:1 in Table 1-1, and a heavy chain amino acid sequence of SEQ ID NO:2 in Table 1-2. In other embodiments, the VLA-4 antibody is a variant of one of these antibodies. For example, in some embodiments, the light chain of the antibody has an amino acid sequence that differs by one or more amino acid residues, but not more than 2, 3, 4, 5, or 6 amino acid residues from the sequence of SEQ ID NO:1, and/or the heavy chain of the antibody has an amino acid sequence that differs by one or more amino acid residues, but not more than 2, 3, 4, 5, or 6 amino acid residues from the sequence of SEQ ID NO:2.

A "difference" in amino acid sequence, as used in this context, means a difference in the identity of an amino acid (e.g., a substitution of a different amino acid for an amino acid in SEQ ID NO:7 or 11 referred to above) or a deletion or insertion. A difference can be, for example, in a framework region, a CDR, a hinge, or a constant region. A difference can be internal or at the end of a sequence of protein. In some embodiments, some or all differences are conservative changes as compared to the recited sequence.

In certain embodiments, the pH of the composition is about 6.0±0.5 (e.g., about 5.0±0.5, about 6.0±0.5, about 7.0±0.5), and the phosphate buffer composition is between about 5 mM and about 30 mM (e.g., about 10 mM, about 15 mM, about 20 mM, about 25 mM). In another embodiment, the composition further comprises a salt, such as sodium chloride, at a concentration of between about 100 mM and about 200 mM (e.g., about 120 mM, 140 mM, 160 mM, 180 mM). In another embodiment, the composition comprises L-arginine hydrochloride, or glycerol. In another embodiment, the composition contains an amino acid, such as glycine, at a concentration of about 200 mM to about 300 mM (e.g., about 220 mM, 240 mM, 260 mM, 280 mM). In another embodiment, the composition contains a pharmaceutically acceptable excipient, such as a surfactant, such as polysorbate 80, in an amount of about 0.001% to about 2.0%, about 0.004% to about 0.4%, about 0.008 to about 0.2%, about 0.02% to about 0.08% (w/v) (e.g., about 0.01%, about 0.02%, about 0.03%, about 0.04%, about 0.05%, about 0.06%, about 0.07%, about 1%, about 1.5%).

In certain embodiments, the composition includes glycerol, and contains substantially no L-arginine hydrochloride, or sodium chloride. In other embodiments, the composition includes L-arginine hydrochloride, but substantially no glycerol or sodium chloride (other than that from the phosphate buffer and the L-arginine hydrochloride). In other embodiments, the composition includes sodium chloride, but substantially no glycerol or L-arginine hydrochloride.

In some embodiments, the antibody formulation includes a histidine buffer, e.g., instead of a phosphate buffer, and the histidine buffer is about pH 5 to about pH 7 (e.g., about pH 5.5±0.5, pH 6±0.5, or pH 6.5±0.5). The histidine buffer composition is between about 10 mM and about 30 mM (e.g., about 15 mM, about 20 mM, about 25 mM). The histidine buffer formulation also includes about 200 mM to about 300 mM glycerol (e.g., about 240 mM, about 250 mM, about 260 mM, about 270 mM, about 280 mM glycerol), and polysorbate 80 to about 0.001% to about 2.0% (w/v) (e.g., about 0.02%, about 0.03%, about 0.04%, about 0.05%, about 0.06%, about 0.07%, about 1%, about 1.5%). The histidine formulation optionally includes about 5 mM to about 15 mM L-methionine (e.g., about 10 mM L-methionine).

In one embodiment, a composition featured herein contains 140 mg/mL to 160 mg/mL natalizumab, 5 mM to 15 mM sodium phosphate buffer, 130 mM to 150 mM sodium chloride, and 0.01% to 0.1% (w/v) polysorbate 80, at pH 6±0.5. In another embodiment, the composition contains 140 mg/mL to 160 mg/mL natalizumab, 5 mM to 15 mM sodium phosphate buffer, 250 mM to 300 mM glycerol, and 0.01% to 0.1% (w/v) polysorbate 80, at pH 6±0.5. In yet another embodiment, the composition contains 140 mg/mL to 160 mg/mL natalizumab, 5 mM to 15 mM sodium phosphate buffer, 150 mM to 170 mM L-arginine hydrochloride, and 0.01% to 0.1% (w/v) polysorbate 80, at pH 6±0.5.

In one embodiment, the composition featured herein is a liquid.

In another embodiment, the composition is stable for at least 12 months (e.g., at least 24, 30, 36 months), at a temperature of about 2° C. to about 8° C. (e.g., about 5° C.). In another embodiment, the composition is stable for at least 2, 3, 4, 5, 6, or 7 days (e.g., at least one week or 12 or 14 days). at ambient temperature (about 20-30° C., such as about 25° C.).

In yet another embodiment, the composition is suitable for SC or IM administration. In even another embodiment, the composition is suitable for IV administration.

In another aspect, the invention features a method of preparing an aqueous composition, such as a stable aqueous composition, that includes about 120 to about 190 mg/mL VLA-4 binding antibody and polysorbate in a phosphate buffer. The method includes expressing the antibody in cell culture, passing the antibody through at least one chromatography purification step, passing the antibody through at least two ultrafiltration/diafiltration steps in phosphate buffer, passing the antibody through at least one ultrafiltration step in phosphate buffer, and adjusting the concentration of the antibody, e.g., downward, to about 120 mg/mL to about 190 mg/mL, by adding polysorbate and/or phosphate buffer. In one embodiment, the VLA-4 binding antibody is natalizumab, and in another embodiment the polysorbate is polysorbate 80. The concentration of the antibody can be, e.g., about 135 mg/mL to about 165 mg/mL, e.g., about 150 mg/mL. In some embodiments, the phosphate buffer includes other excipients such as glycerol, L-arginine hydrochloride, or sodium chloride. The final formulation has a pH of about 5 to about 7, e.g., from about 5.5 to about 6.5.

In another aspect, the invention features a delivery device designed for or suitable for SC or IM administration, where the delivery device is packaged with or contains a unit dose of a composition described herein, e.g., a composition containing a concentrated formulation of natalizumab suitable for SC or IM administration. In one embodiment, the unit dose is about 100 mg to about 450 mg (e.g., about 120 mg to about 350 mg; about 150 mg, about 200 mg, about 250 mg, about 300 mg). In one embodiment, the unit dose ranges from greater than about 100 mg to about 450 mg. In another embodiment, the unit dose will deliver between about 1.4 mg/kg and about 3.0 mg/kg VLA-4 binding antibody or fragment thereof per kg of body weight to the human. In another embodiment, the unit dose is about 0.25 mL to about 1.5 mL (e.g., about 0.5 mL, about 0.75 mL, about 1.0 mL).

In one embodiment, a unit dose is about 300 mg natalizumab, and in another embodiment, the unit dose is divided into fractions, such as into two halves, each half containing about 150 mg of a VLA-4 binding antibody. In yet another embodiment, a patient is administered natalizumab as a regimen. In one embodiment, the patient is administered about 300 mg natalizumab once per month, e.g., by the administration of two sequential doses of 150 mg natalizumab. In an alternative embodiment, the patient is administered about 300 mg natalizumab per month, administered by a first dose of 150 mg natalizumab, then a second dose of 150 mg natalizumab about two weeks later.

The invention features methods that optimize provision of a highly concentrated liquid formulation of a VLA-4 binding antibody, e.g., natalizumab, to a patient.

In one embodiment, the method allows for a gradual increase in the concentration of the antibody provided. This allows ramp-up of antibody concentration and can allow monitoring of the patient for tolerance, reactions and the like as the concentration is increased. For example, the method can start by providing natalizumab to the patient at one or more initial or relatively low concentrations followed by providing natalizumab to the patient at a final, higher concentration. Exemplary formulations for the initial concentration will typically have an antibody concentration of less than 80%, 70%, 50%, 30%, 20% or 10% of the final higher concentration. Typical initial concentrations can be, e.g., 20 mg/mL, 30 mg/mL, or 40 mg/mL. Typical final concentrations will be, e.g., about 120 mg/mL to about 190 mg/mL (e.g., about 135 mg/mL, about 140 mg/mL, about 150 mg/mL, about 160 mg/mL, or about 165 mg/mL). In some embodiments, the patient will receive one, or a plurality of administrations at one or a plurality of initial concentrations. For example, in one embodiment, the patient will receive increasing concentrations over a number of administrations. In some embodiments, the patient will receive 2, 3, 4, 5, 6, 7, or 8 administrations at one or more initial concentrations prior to reaching the final concentration. For example, the patient will receive one or more administrations at a first initial concentration, and one or more administrations at a second higher concentration. In some embodiments, the patient is assessed after one or more administrations for symptoms, including adverse symptoms. In some embodiments, the patient is administered a formulation having an increased concentration of natalizumab only after determining that the patient does not have an unacceptable adverse reaction to the previous administration.

In one embodiment, the method allows for a gradual increase in the antibody dosage provided (dosage as used here refers to the amount of antibody provided in one, or in each of a defined small number, e.g., 2, administrations). This allows ramp-up of dosage and can allow monitoring of the patient for tolerance, adverse reactions, and the like as the dosage is increased. For example, the method can begin by providing natalizumab to the patient at one or more initial or relatively low dosages followed by providing natalizumab to the patient at a final, higher dosage. Typical initial dosages can be, e.g., 80%, 70%, 50%, 30%, 20% or 10% or less of the final higher dosage. Typical final dosages will vary based on the frequency of administration once steady state administration has been achieved. For example, some embodiments include final dosages of between 75 mg and 500 mg (e.g., 100 mg, 150 mg, 200 mg, 250 mg, 300 mg, 350 mg, 400 mg, 450 mg) (these dosages can be typical of approximately monthly administration). Other embodiments include final dosages of between 50 mg and 250 mg (e.g., 75 mg, 100 mg, 150 mg, 200 mg) (these dosages are typical of administration every two weeks). Other embodiments include final dosages of between 25 mg and 150 mg (e.g., 50 mg, 75 mg, 100 mg, 125 mg) (these dosages are typical of weekly administration). In some embodiments, the patient will receive one or a plurality of administrations, at one or a plurality of initial dosages. For example, in one embodiment, the patient will receive increasing dosages over a number of administrations. In some embodiments, the patient will receive 2, 3, 4, 5, 6, 7, or 8 administrations at one or more initial dosages prior to reaching the final dosage. For example, the patient will receive one or more administrations at a first initial dosage, and one or more administrations at a second higher initial dosage. In some embodiments, the patient is assessed after one or more administrations for symptoms, including adverse symptoms. In some embodiments, the patient is administered an increased dosage of natalizumab only after determining that the patient does not have an unacceptable adverse reaction to the previous dosage.

The invention also includes kits, e.g., starter packs, for implementing a ramp-up of concentration or dosage. In one embodiment, the patient, or a healthcare provider, is provided with a kit or "starter pack" of natalizumab formulations, including packages of increasing concentrations or dosages of natalizumab. The patient or healthcare provider provided with a starter pack is instructed to self-administer or administer a first, e.g., a low, or the lowest dosage or concentration of natalizumab, and to wait a designated period time. If the patient experiences no, or a minor level of, adverse symptoms, the patient or health care provider is instructed to self-administer or administer a second formulation, e.g., a higher, e.g., the next highest concentration or dosage. The patient or healthcare provider is instructed to continue the step-wise increase in dosages or concentrations until the desired dosage or concentration is achieved. The patient or healthcare provider may be instructed to maintain self-administration or administration of the final formulation at regular intervals for a specified period of time.

In one embodiment, the highly concentrated formulation of VLA-4 binding antibody is provided to a patient prepacked in a suitable delivery device, such as a syringe.

In another aspect, the invention features a method, e.g., a method of instructing a patient in need of a VLA-4 binding antibody therapy, how to administer a formulation described herein. The method includes (i) providing the patient with at least one unit dose of a highly concentrated formulation of VLA-4 binding antibody described herein; and (ii) instructing the patient to self-administer the at least one unit dose intramuscularly or subcutaneously. Another method, e.g., a method of treatment, includes (i) providing the patient with at least two unit doses of a highly concentrated formulation of VLA-4 binding antibody; and (ii) instructing the patient to self-administer the unit doses subcutaneously or intramuscularly, e.g., one dose at a time.

In one embodiment, the patient has an inflammatory disorder, such as multiple sclerosis. In other embodiments, the patient has, e.g., asthma (e.g., allergic asthma), an arthritic disorder (e.g., rheumatoid arthritis, psoriatic arthritis), diabetes (e.g., type I diabetes), a fibrotic disorder (e.g., pulmonary fibrosis, myelofibrosis, liver cirrhosis, mesangial proliferative glomerulonephritis, crescentic glomerulonephritis, diabetic nephropathy, renal interstitial fibrosis), or an inflammatory bowel disorder (e.g., Crohn's disease, ulcerative colitis).

Another aspect, the invention features a unit dose of a concentrated formulation of VLA-4 binding antibody described herein, where the unit dose is about 0.25 mL to about 1.5 mL (e.g., about 0.5 mL, about 0.75 mL, or about 1.0 mL). In one embodiment, a unit dose is about 100 mg to about 450 mg (e.g., about 150 mg, about 160 mg, about 180 mg, about 200 mg, about 250 mg, about 300 mg, or about 350 mg).

In another aspect, the invention features a unit dose of an aqueous formulation of VLA-4 binding antibody, where administration of the unit dose to a human will deliver between about 1.4 mg and about 3.0 mg VLA-4 binding antibody or fragment thereof per kg of body weight to the human.

In another aspect, the invention features a method of treating a patient by administering to the patient a composition containing a VLA-4 binding antibody in a formulation suitable for SC or IM administration. In one embodiment, the patient has an inflammatory disorder, such as multiple sclerosis, asthma, rheumatoid arthritis, diabetes, or Crohn's disease. In another embodiment, the composition is administered as a regimen. In another embodiment, the method further includes selecting a patient suitable for treatment with the composition. A patient suitable for treatment, for example, has demonstrated a sign or symptom indicative of disease onset, such as a sign or symptom indicative of MS. In yet another embodiment, the method further includes administering to the patient a second therapeutic agent, such as, a thrombolytic agent, a neuroprotective agent, an anti-inflammatory agent, a steroid, a cytokine, or a growth factor.

In another aspect, the invention features a method of evaluating a patient by determining if the patient meets a preselected criterion, and if the patient meets the preselected criterion approving, providing, prescribing, or administering a VLA-4 binding antibody formulation described herein to the patient. In one embodiment, the preselected criterion is the failure of the patient to adequately respond to a prior alternate therapeutic treatment or regimen, e.g., for treatment of MS. In another embodiment, the preselected criterion is the absence of any signs or symptoms of progressive multifocal leukoencephalopathy (PML), or the absence of any diagnosis of PML. In another embodiment, the criterion is as described in U.S. Ser. No. 60/836,530, filed Aug. 9, 2006, hereby incorporated by reference, which describes methods and systems for drug distribution.

In another aspect, the invention features a method of instructing a recipient on the administration of a highly concentrated formulation of natalizumab. The method includes instructing the recipient (e.g., an end user, patient, physician, retail or wholesale pharmacy, distributor, or pharmacy department at a hospital, nursing home clinic or HMO) that the drug should be administered to a patient subcutaneously or intramuscularly.

In another aspect, a method of distributing a composition described herein is provided. The composition contains a highly concentrated formulation of natalizumab and is suitable for subcutaneous or intramuscular or intravenous administration. The method includes providing a recipient (e.g., an end user, patient, physician, retail or wholesale pharmacy, distributor, or pharmacy department at a hospital, nursing home clinic or HMO) with a package containing sufficient unit dosages of the drug to treat a patient for at least 6, 12, 24, or 36 months.

In another aspect, the invention features a method of evaluating the quality of a package or lot of packages (e.g., to determine if it has expired) of a composition described herein containing a highly concentrated amount of VLA-4 binding antibody. The method includes evaluating whether the package has expired. The expiration date is at least 6, 12, 24, 36, or 48 months, e.g., greater than 24 or 36 months, from a preselected event, such as manufacturing, assaying, or packaging. In some embodiments, a decision or step is taken as a result of the analysis, e.g., the antibody in the package is used or discarded, classified, selected, released or withheld, shipped, moved to a new location, released into commerce, sold, or offered for sale, withdrawn from commerce or no longer offered for sale, depending on whether the product has expired.

In another aspect, the invention features a package containing at least 2 unit doses of an aqueous composition containing a highly concentrated amount of VLA-4 binding antibody. In one embodiment, all of the unit doses contain the same amount of antibody, and in other embodiments, there are unit dosages of two or more strengths, or two or more different formulations, e.g., having different strengths or release properties). In one embodiment, at least one dosage contains about 100 mg to about 450 mg of VLA-4 binding antibody, e.g., about 100 mg, about 200 mg, about 250 mg, about 300 mg, about 350 mg, or about 400 mg of VLA-4 binding antibody.

In another aspect, the invention includes a method of instructing a recipient on the administration of an aqueous formulation containing VLA-4 binding antibody. The method includes instructing the recipient (e.g., an end user, patient, physician, retail or wholesale pharmacy, distributor, or pharmacy department at a hospital, nursing home clinic or HMO) that the antibody should be administered to a patient prior to the expiration date. The expiration date is at least 6, 12, 18, 24, 36, or 48 months, e.g., greater than 18, 24 or 36 months, from a preselected event, e.g., manufacturing, assaying, or packaging. In one embodiment, the recipient also receives a supply of the antibody, e.g., a supply of unit dosages.

In another aspect, the invention features the use of a method or system described in PCT/US2007/075577 (published as WO/2008/021954) with a formulation described herein. Embodiments include a method of distributing a formulation described herein, monitoring or tracking the provision of a formulation described herein to a pharmacy, infusion center, or patient, monitoring one or more patients, selecting patients, or compiling or reporting data on the use of a formulation described herein. PCT/US2007/075577 (published as WO/2008/021954) is hereby incorporated by reference.

In another aspect, the invention features a method of selecting a patient for treatment with a formulation described herein for a disorder described herein, e.g., multiple sclerosis. The method includes:
selecting or providing a patient who has been treated by intravenous delivery of a VLA-4 binding antibody, e.g., natalizumab; and
providing or administering a formulation described herein to the patient,
thereby treating the patient.

In another aspect, the invention features a method of analyzing a product or a process, e.g., a manufacturing process. The method includes providing an aqueous formulation of a highly concentrated VLA-4 binding antibody composition, e.g., one made by a process described herein, and providing an evaluation of the formulation by assessing a solution parameter, such as color (e.g., colorless to slightly yellow, or colorless to yellow), clarity (e.g., clear to slightly opalescent or clear to opalescent), or viscosity (e.g., between approximately 5 cP and 30 cP (e.g., 10 cP, 20 cP) when measured at ambient temperature, such as at 20° C.-30° C., e.g., 25° C.). The evaluation can include an assessment of one or more solution parameters. Optionally, a determination of whether the solution parameter meets a preselected criteria is determined, e.g., whether the preselected criteria is present, or is present in a preselected range, is determined, thereby analyzing the process.

In one embodiment, evaluation of the process includes a measure of the stability of the anti-VLA-4 antibody formulation. Stability of the antibody formulation can be measured, for example, by aggregate formation, which is assayed, e.g., by size exclusion high pressure liquid chromatography (HPLC), by color, clarity, or viscosity as described herein. A formulation can be determined to be stable, and therefore acceptable for further processing or distribution, if the change in an assay parameter is less than about 10%, 5%, 3%, 2%, 1%, 0.5%, 0.05%, or 0.005% or less, over a pre-set period of time, and optionally at a given temperature. In one embodiment, a highly concentrated liquid anti-VLA-4 antibody formulation is stable for 1, 2, 3, 4, or 5 days or more at room temperature (e.g., at about 18° C., 19° C., 20° C., 21° C., 22° C., 23° C., 24° C., or 25° C.).

In one embodiment, the method further includes comparing the value determined with a reference value, to thereby analyze the manufacturing process.

In one embodiment, the method further includes maintaining the manufacturing process based, at least in part, upon the analysis. In one embodiment, the method further includes altering the manufacturing process based upon the analysis.

In another embodiment the method includes evaluating a process, e.g., manufacturing process, of an aqueous formulation of highly concentrated VLA-4 binding antibody made by a selected process, that includes making a determination about the process based upon a method or analysis described herein. In one embodiment, the method further includes maintaining or altering the manufacturing process based, at least in part, upon the method or analysis. Thus, in another embodiment the party making the evaluation does not practice the method or analysis described herein but merely relies on results which are obtained by a method or analysis described herein.

In another embodiment the method includes comparing two or more preparations in a method of monitoring or controlling batch-to-batch variation or to compare a preparation to a reference standard.

In yet another embodiment, the method can further include making a decision, e.g., to classify, select, accept or discard, release or withhold, process into a drug product, ship, move to a different location, formulate, label, package, release into commerce, sell or offer for sale the preparation, based, at least in part, upon the determination.

In another aspect, the invention features a method of storing, distributing, or using a VLA-4 binding antibody formulation, e.g., a natalizumab formulation, described herein. The method includes:
storing the formulation for a first period at a first, low temperature, e.g., less than 18° C., e.g., from above freezing but at or below 15° C., 10° C., or 4° C.;
storing the formulation for a second period at a second, higher temperature, e.g., without refrigeration or at room temperature, e.g., between 18° C. and 25° C., wherein said second period is no more than 24, 48, 72, or 96 hours, and where in some embodiments, the second period ends upon administration to the patient or discard of the formulation.

In another aspect, the invention features a method of storing, distributing, or using a VLA-4 binding antibody formulation, e.g., a natalizumab formulation, described herein. The method includes:

storing the formulation at a first, low temperature, e.g., less than 18° C., e.g., from above freezing, but at or below 15° C., 10° C., or 4° C.;

providing the formulation to a recipient, e.g., an end-user, e.g., a patient or healthcare provider;

optionally, instructing the end-user that the formulation can be stored at a second, higher temperature, e.g., without refrigeration or at room temperature, e.g., between 18° C. and 25° C.; and after receipt by the recipient, storing the formulation for up to 24, 48, 72, or 96 hours at the second temperature.

In another aspect, the invention features a method of instructing an entity, e.g., a pharmacy, distributor, or end-user, e.g., a patient or healthcare provider, how to store, distribute, or use a VLA-4 binding antibody formulation, e.g., a natalizumab formulation, described herein. The method includes:

instructing the entity that the formulation should be stored at a first, low temperature, e.g., less than 18° C., e.g., from above freezing but at or below 15° C., 10° C., or 4° C., for a first period, where said first period extends up until the formulation is provided to an end-user or until within 24, 48, 72, or 96 hours prior to administration to a patient; and instructing the entity that the formulation can be stored at a second, higher temperature, e.g., without refrigeration or at room temperature, e.g., between 18° C. and 25° C. for a second period, where said second period does not exceed 24, 48, 72, or 96 hours, thereby instructing an entity.

In another aspect, the invention features a method of storing, distributing, or using a VLA-4 binding antibody formulation, e.g., a natalizumab formulation, described herein. The method includes:

storing the formulation at a first, low temperature, e.g., less than 18° C., e.g., from above freezing but at or below 15° C., 10° C., or 4° C.; and storing the formulation at a second, higher temperature, e.g., without refrigeration or at room temperature, e.g., between 18° C. and 25° C. for no more than 24, 48, 72, or 96 hours.

In another aspect, the invention features a method of evaluating, such as evaluating the quality of, an aqueous formulation of highly concentrated VLA-4 binding antibody, e.g., in a quality control or release specification analysis. The method includes providing an evaluation of an antibody formulation for a solution parameter, such as color (e.g., colorless to slightly yellow, or colorless to yellow), clarity (e.g., clear to slightly opalescent or clear to opalescent), or viscosity (e.g., between approximately 5 cP and 30 cP when measured at ambient temperature, such as at 20° C.-30° C., e.g., 25° C.). The evaluation can include an assessment of one or more of the above parameters. The method also includes, optionally, determining whether the solution parameter meets a preselected criteria, e.g., whether the preselected criteria is present, or is present in a preselected range. If the observed solution parameter is within a preselected range of values, or meets the preselected standard criteria, then the preparation is selected, such as for packaging, use, sale, release into commerce, discarding etc.

In another aspect, the invention features a method of complying with a regulatory requirement, e.g., a post approval requirement of a regulatory agency, e.g., the FDA. The method includes providing an evaluation of an antibody formulation for a solution parameter, such as color (e.g., colorless to slightly yellow, or colorless to yellow), clarity (e.g., clear to slightly opalescent or clear to opalescent), or viscosity (e.g., between approximately 5 cP and 30 cP when measured at ambient temperature, such as at 20° C.-30° C.). The post approval requirement can include a measure of one more of the above parameters. The method also includes, optionally, determining whether the observed solution parameter meets a preselected criteria or if the parameter is in a preselected range; optionally, memorializing the value or result of the analysis, or communicating with the agency, e.g., by transmitting the value or result to the regulatory agency.

In another aspect, the invention features a method of making a batch of an aqueous formulation of VLA-4 binding antibody having a preselected property, e.g., meeting a release specification, label requirement, or compendial requirement, e.g., a property described herein. The method includes providing a test antibody preparation; analyzing the test antibody preparation according to a method described herein; determining if the test antibody preparation satisfies a preselected criteria, e.g., having a preselected relationship with a reference value, e.g., one or more reference values disclosed herein, and selecting the test antibody preparation to make a batch of product.

In another aspect, the invention features multiple batches of an aqueous formulation of VLA-4 binding antibody, wherein one or more solution parameters (e.g., a value or solution parameter determined by a method described herein), for each batch varies less than a preselected range from a pre-selected desired reference value or criteria, e.g., a range or criteria described herein. In some embodiments, one or more parameters for one or more batches of an antibody formulation, is determined and a batch or batches selected as a result of the determination. Some embodiments include comparing the results of the determination to a preselected value or criteria, e.g., a reference standard. Other embodiments include adjusting the dose of the batch to be administered, e.g., based on the result of the determination of the value or parameter.

In another aspect, the invention features a method of one or more of: providing a report to a report-receiving entity, evaluating a sample of an aqueous formulation of VLA-4 binding antibody for compliance with a reference standard, e.g., an FDA requirement, seeking indication from another party that a preparation of the VLA-4 binding antibody meets some predefined requirement, or submitting information about a preparation of a VLA-4 binding antibody to another party. Exemplary receiving entities or other parties include a government, e.g., the U.S. federal government, e.g., a government agency, e.g., the FDA. The method includes one or more (or all) of the following steps for making and/or testing an aqueous formulation of VLA-4 binding antibody in a first country, e.g., the U.S.; sending at least an aliquot of the sample outside the first country, e.g., sending it outside the United States, to a second country; preparing, or receiving, a report which includes data about the structure of the preparation of the VLA-4 binding antibody, e.g., data related to a structure and/or chain described herein, e.g., data generated by one or more of the methods described herein; and providing said report to a report recipient entity.

In one embodiment, the report-receiving entity can determine if a predetermined requirement or reference value is met by the data and, optionally, a response from the report-receiving entity is received, e.g., by a manufacturer, distributor or seller of an aqueous formulation of a VLA-4 binding antibody. In one embodiment, upon receipt of approval from the report recipient entity, the preparation of VLA-4 binding antibody is selected, packaged, or placed into commerce.

In another aspect, the invention features a method of evaluating an aqueous formulation of VLA-4 binding antibody. The method includes receiving data with regard to the presence or level of VLA-4 binding antibody, e.g., wherein the data was prepared by one or more methods described herein; providing a record which includes said data and optionally includes an identifier for a batch of VLA-4 binding antibody; submitting said record to a decision-maker, e.g., a government agency, e.g., the FDA; optionally, receiving a communication from said decision maker; optionally, deciding whether to release or market the batch of VLA-4 binding antibody based on the communication from the decision maker. In one embodiment, the method further includes releasing the sample.

Exemplary formulations include the following:

1. Natalizumab at 125-175 mg/mL, or 140-160 mg/mL, e.g., 150 mg/mL;
   sodium phosphate buffer at 1-100 mM, 5-20 mM, or 5-50 mM, e.g., 10 mM;
   sodium chloride at 50-200 mM, 100-180 mM, or 120-160 mM, e.g., 140 mM;
   polysorbate 80 at 0.01-0.12%, 0.02-0.08%, or 0.02-0.06%, e.g., 0.04% (w/v), and
   pH 6.0±1.0, e.g., 6.0±0.5;
2. Natalizumab at 125-175 mg/mL or 140-160 mg/mL, e.g., 150 mg/mL;
   10 mM sodium phosphate buffer;
   140 mM sodium chloride;
   0.04% (w/v) polysorbate 80 and
   pH 6.0±0.5;
3. 150 mg/mL Natalizumab;
   sodium phosphate buffer at 1-100 mM, 5-20 mM, or 5-50, e.g., 10 mM;
   140 mM sodium chloride;
   0.04% (w/v) polysorbate 80; and
   pH 6.0±0.5;
4. 150 mg/mL Natalizumab;
   10 mM sodium phosphate buffer;
   sodium chloride at 50-200 mM, 100-180 mM, or 120-160 mM, e.g., 140 mM;
   0.04% (w/v) polysorbate 80 and
   pH 6.0±0.5;
5. 150 mg/mL Natalizumab;
   10 mM sodium phosphate buffer;
   140 mM sodium chloride;
   polysorbate 80 at 0.01-0.12%, 0.02-0.08%, or 0.02-0.06%, e.g., 0.04% (w/v), and
   pH 6.0±0.5;
6. 150 mg/mL Natalizumab;
   10 mM sodium phosphate buffer;
   140 mM sodium chloride;
   0.04% (w/v) polysorbate 80 and
   pH 6.0±1.0, e.g., pH 6.0±0.5; and
7. 150 mg/mL Natalizumab;
   10 mM sodium phosphate buffer;
   140 mM sodium chloride;
   0.04% (w/v) polysorbate 80; and
   pH 6.0±0.5.

In some embodiments, any of the above formulations 1-7 can be essentially free of an amino acid, e.g., arginine or glycine, or glycerol.

Methods and compositions disclosed herein can be used where the presence, distribution, or amount, of one or more structures in the mixture may possess or impinge on the biological activity. The methods are also useful from a structure-activity prospective, to evaluate or ensure biological equivalence.

A "highly concentrated VLA-4 binding antibody formulation" as used herein, refers to a stable aqueous formulation containing between about 120 mg/mL to about 190 mg/mL (e.g., about 120 mg/mL, 130 mg/mL, 140 mg/mL, 150 mg/mL, 160 mg/mL, 170 mg/mL, 180 mg/mL, 190 mg/mL) VLA-4 binding antibody, such as natalizumab.

"Suitable for SC or IM administration" means that administration of the composition to a subject, such as a human, will have a therapeutic effect, such as to improve one or more symptoms in the subject.

The term "treating" refers to administering a therapy in an amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject.

A "stable" formulation of VLA-4 binding antibody exhibits little or no signs of any one or more of aggregation, fragmentation, deamidation, oxidation, or change in biological activity over an extended period of time, e.g., 12 months, 24 months, 36 months or longer. For example, in one embodiment, less than 10% of the composition is aggregated, fragmented, or oxidized. Aggregation, precipitation, and/or denaturation can be assessed by known methods, such as visual examination of color and/or clarity, or by UV light scattering or size exclusion chromatography. The ability of the protein to retain its biological activity can be assessed by detecting and quantifying chemically altered forms of the antibody. Size modification (e.g., clipping), which can be evaluated using size exclusion chromatography, SDS-PAGE and/or matrix-assisted laser desorption ionization/time-of-flight mass spectrometry (MALDI/TOF MS), or peptide mapping of endoproteinase-treated antibody, for example. Other types of chemical alteration include charge alteration (e.g., occurring as a result of deamidation), which can be evaluated by ion-exchange chromatography, for example. An antibody "retains its biological activity" in a pharmaceutical formulation, if the biological activity of the antibody at a given time is within about 10% of the biological activity exhibited at the time the pharmaceutical formulation was prepared as determined in an antigen binding assay, for example.

A "VLA-4 binding antibody" refers to an antibody that binds to a VLA-4 integrin, such as to the α4 subunit of the VLA-4 integrin, and at least partially inhibits an activity of VLA-4, particularly a binding activity of a VLA-4 integrin or a signaling activity, e.g., ability to transduce a VLA-4 mediated signal. For example, a VLA-4 binding antibody may inhibit binding of VLA-4 to a cognate ligand of VLA-4, e.g., a cell surface protein such as VCAM-1, or to an extracellular matrix component, such as fibronectin or osteopontin. A VLA-4 binding antibody may bind to either the α4 subunit or the β1 subunit, or to both. In one embodiment, the antibody binds to the B1 epitope of α4. A VLA-4 binding antibody may bind to VLA-4 with a $K_d$ of less than about $10^{-6}$, $10^{-7}$, $10^{-8}$, $10^{-9}$, or $10^{-10}$ M. VLA-4 is also known as alpha4/beta1 and CD29/CD49b.

As used herein, the term "antibody" refers to a protein that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$ fragments, Fd fragments, Fv fragments, and dAb fragments) as well as complete antibodies, e.g., intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FRs and CDRs has been precisely defined (see, Kabat, E. A., et al. (1991) *Sequences of Proteins of Immunological Interest, Fifth Edition*, U.S. Department of Health and Human Services, NIH Publication No. 91-3242; and Chothia, C. et al. (1987) *J. Mol. Biol.* 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with VLA-4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human (HC, heavy chain; LC, light chain). Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762. In some cases, humanized immunoglobulins can include a non-human amino acid at one or more framework amino acid positions.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody refers to one or more fragments of a full-length antibody that retain the ability to specifically bind to a target of interest, e.g., VLA-4. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad. Sci.* USA 85:5879-5883.

As used herein, "about" refers to within 0.1% to 5% of the given value (e.g., within 5%, 3%, 2%, 1%, 0.5%, 0.1% above or below the given value). Where amounts and other designated values are provided herein, the allowable deviation is within pharmaceutically acceptable standards.

Certain advantages are provided by embodiments of the invention. In some cases, it is difficult to make high concentration formulations of proteins, e.g., antibodies, for use in pharmaceutical compositions. Methods of preparing such formulations are presented herein. Pharmaceutical compositions containing high concentrations of protein, e.g., of anti-VLA-4 antibody, can be useful for administration over a shorter time frame. A high concentration formulation, e.g., of anti-VLA-4 antibody, can also be administered by simplified methods (e.g., subcutaneously).

The details of one or more embodiments of the invention are set forth in the accompanying drawings and the description below. Other features, objects, and advantages of the invention will be apparent from the description and drawings, and from the claims.

DETAILED DESCRIPTION

Figure 1:
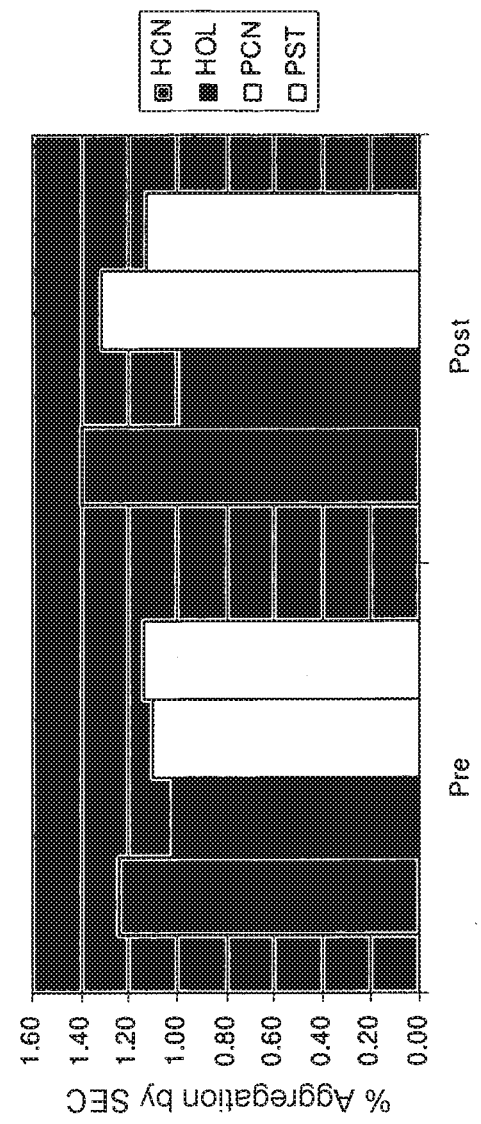
FIG. 1 shows the level of soluble aggregates pre- and post-agitation of a natalizumab at a concentration of 150 mg/mL in various formulations. HCN=20 mM histidine, 240 mM glycine, 0.04% (w/v) polysorbate 80, pH 6. HOL=20 mM histidine, 240 mM glycerol, 0.04% (w/v) polysorbate 80, pH 6. PCN=20 mM phosphate, 240 mM glycine, 0.02% (w/v) polysorbate 80, pH 6. PST=20 mM phosphate, 140 mM NaCl, 0.02% (w/v) polysorbate 80, pH 6.

Stable formulations of highly concentrated VLA-4 binding antibody, are useful for subcutaneous (SC), intramuscular (IM), or intravenous (IV) administration. The formulations featured in the invention contain from about 120 mg/mL to about 190 mg/mL VLA-4 binding antibody, such as natalizumab.

Pharmaceutical Compositions

The compositions described herein are formulated as pharmaceutical compositions. VLA-4 binding antibody (e.g., natalizumab) can be provided, for example, in a buffered solution at a concentration between about 120 mg/mL and 190 mg/mL (e.g., between about 120 mg/mL and about 180 mg/mL, between about 140 mg/mL and about 160 mg/mL, between about 135 mg/mL and about 165 mg/mL; e.g., about 120 mg/mL, 130 mg/mL, 135 mg/mL, 140 mg/mL, 150 mg/mL, 160 mg/mL, 165 mg/mL, 170 mg/mL, 180 mg/mL, 190 mg/mL). In one embodiment, the VLA-4 binding antibody (e.g., natalizumab) is provided in a buffered solution at a concentration greater than 150 mg/mL and less than about 190 mg/mL. In another embodiment, the formulation is prepared at a higher concentration (e.g., 170 mg/mL to 190 mg/mL), and then diluted back to the desired concentration (e.g., 135 mg/mL to 165 mg/mL). For example, the formulation can be prepared with an antibody concentration of, e.g., 175 mg/mL, 180 mg/mL or 185 mg/mL, and then diluted back to a concentration desired for administration, e.g., 140 mg/mL, 145 mg/mL, 150 mg/mL, 155 mg/mL, or 160 mg/mL. The composition can be stored at 2-8° C. (e.g., 4° C., 5° C., 6° C., 7° C.).

In one embodiment, the VLA-4 binding antibody can be formulated with excipient materials, such as 160 mM L-arginine hydrochloride (±10%), a phosphate buffer (e.g., sodium dibasic phosphate heptahydrate and sodium monobasic phosphate), and polysorbate 80, where the total sodium content does not exceed 60 mM. In another embodiment, VLA-4 binding antibody can be formulated with 275 mM glycerol (±10%), a phosphate buffer (e.g., sodium dibasic phosphate heptahydrate and sodium monobasic phosphate or other phosphate salts), and polysorbate 80, and is substantially free of sodium chloride. In another embodiment, VLA-4 binding antibody can be formulated with 140 mM sodium chloride (±10%), a phosphate buffer, and polysorbate 80. Exemplary formulations that include phosphate buffers are provided below, e.g., at examples 8, 9, 10, 11, and 12.

In one embodiment, the VLA-4 binding antibody can be formulated with excipient materials, such as 240 mM glycerol (±10%), a histidine buffer, polysorbate 80, and optionally L-methionine. Exemplary formulations that include histidine buffers are provided below, e.g., at examples 13 and 14.

Phosphate buffers are known in the art and include, e.g., aqueous solutions of sodium phosphate dibasic (anhydrous), sodium phosphate dibasic heptahydrate, sodium phosphate dibasic dihydrate, sodium phosphate monobasic anhydrous, sodium phosphate monobasic monohydrate, sodium phosphate monobasic dihydrate, sodium phosphate tribasic anhydrous, or sodium phosphate tribasic dodecahydrate, brought to the proper pH. Phosphate buffers also include, e.g., potassium phosphate monobasic, potassium phosphate dibasic anhydrous, or potassium phosphate tribasic, brought to the proper pH.

Histidine buffers are known in the art and include, e.g., aqueous solutions of D-histidine, D-histidine monochloride monohydrate, DL-histidine, DL-histidine monochloride monohydrate, L-histidine, or L-histidine monochloride monohydrate, brought to the proper pH with either hydrochloric acid or sodium hydroxide, or other acid or base known in the art.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible.

A "pharmaceutically acceptable salt" refers to a salt that retains the desired biological activity of the antibody and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, free amino acids, and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Typically physiologically compatible agents, such as free amino acids, the hydrochloride salts, sodium salts, or potassium salts of free amino acids are used as excipients in pharmaceutical formulations to promote stability of the antibody. The formulations herein can include additives such as glycerol, mannitol, sorbitol, and other polyols, as well as sugars (e.g., sucrose), to promote stability.

The formulations featured herein can include a pharmaceutically acceptable excipient, such as a surfactant, e.g., polysorbate 80, glycerin monostearate, polyoxyl stearate, lauromacrogol, or sorbitan oleate. In one embodiment, the formulations featured herein include about 0.01% (w/v) to about 0.1% (w/v) polysorbate 80, e.g., about 0.2% or 0.04% polysorbate 80.

The pharmaceutical compositions containing highly concentrated VLA-4 binding antibodies are in the form of a liquid solution (e.g., injectable and infusible solutions). Such compositions can be administered by a parenteral mode (e.g., subcutaneous, intraperitoneal, or intramuscular injection). The phrases "parenteral administration" and "administered parenterally" as used herein mean modes of administration other than enteral and topical administration, usually by injection, and include, subcutaneous or intramuscular administration, as well as intravenous, intracapsular, intraorbital, intracardiac, intradermal, intraperitoneal, transtracheal, subcuticular, subcapsular, subarachnoid, intraspinal, epidural and intrasternal injection and infusion. In one embodiment, the formulations described herein are administered subcutaneously.

Pharmaceutical compositions are sterile and stable under the conditions of manufacture and storage. A pharmaceutical composition can also be tested to insure it meets regulatory and industry standards for administration.

A pharmaceutical composition containing a highly concentrated amount of VLA-4 binding antibody can be formulated as a solution, microemulsion, dispersion, liposome, or other ordered structure suitable to high antibody concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some embodiments, parameters that describe the formulations, e.g., parameters that may appear on the product label, are characterized. Such parameters include, e.g., color (typically colorless to slightly yellow, or colorless to yellow), clarity (typically clear to slightly opalescent, or clear to opalescent), and viscosity (typically between about 5 cP and 30 cP when measured at ambient temperature, such as at 20° C. to 30° C.). Such parameters can be measured by methods known in the art. For example, clarity can be measured using commercially available opalescence standards (available from, e.g., HunterLab Associates, Inc. (Reston, Va.)).

In some embodiments, the stability of the antibody formulations is assayed. Exemplary methods include, for example, aggregation studies, oxidation studies, fragmentation studies, sialylation studies, isoelectric point studies, half-antibody studies, heavy and light chain parity studies, and analysis of secondary structure (e.g., by circular dichroism), thermal denaturation (e.g., by circular dichroism of differential scanning calorimetry), tryptophan environment (e.g., by fluorescence), IgG fold (e.g., by far UV circular dichroism), and aromatic residue environment (e.g., by UV-Vis spectrophotometry).

Methods of Making Antibody Formulations

Formulations containing VLA-4 binding antibody formulations can be made as described in U.S. Published Application 2005/0053598, modified to accommodate high concentrations of antibody (e.g., concentrations of about 75 mg/mL to about 190 mg/mL, 100 mg/mL to about 180 mg/mL, about 120 mg/mL to about 170 mg/mL, 135 mg/mL to about 165 mg/mL). The process can be altered as would be known to the skilled artisan, but generally would follow a procedure such as the following. Obtain an ampoule from a working cell bank containing cells that make the antibody or protein of interest. Prepare an inoculum. Culture or ferment the cells of the inoculum with additional feedings as is necessary. Harvest/clarify the cells by centrifugation and/or filtration. This can be done for example by concentrating the cells 10 fold by, e.g., spiral wound filtration. Intermediate filtration, such as through a 0.2 μm filter, is followed by, e.g., affinity chromatography, such as by a protein A Sepharose Fast Flow®, and then reverse elution. The antibody containing composition then receives a treatment at low pH, such as at pH 3.6-3.7. The mixture then receives a viral filtration followed by a concentration/diafiltration step. The composition is further purified by, e.g., anion exchange chromatography, such as by DEAE Sepharose Fast Flow®. This step can be performed multiple times. From this point, the composition is then further concentrated and then purified, e.g., by gel filtration chromatrography, such as through a Sephacryl S300HR® system. The antibody containing composition can be further concentrated if so desired. The final formulation is produced by adding buffer and polysorbate, and concentrating the antibody again through an ultrafiltration process. The resulting antibody formulation can be quality control tested and quality assurance (QA) released. An antibody formulation can be produced according to any of the methods exemplified in Table 1 below. For example, the formulation containing a VLA-4 binding antibody, such as natalizumab, can be produced by the following process. A large batch of cell culture, such as from 5,000 to 20,000 Liters (e.g., 5,000; 10,000; 15,000; 20,000 Liters) is inoculated, cultured, fed, harvested and clarified as known in the art. The clarified material is purified e.g., by chromatography, viral inactivation, and viral filtration. Ultrafiltration/diafiltration (UF/DF) of the clarified material results in a phosphate process intermediate. The phosphate process intermediate may be stored at 2-8° C., e.g., for future processing, such as by methods to further concentrate the protein. To make the final formulation, polysorbate and buffer (as described herein) are added to the phosphate process intermediate to achieve the final desired antibody concentration. In one alternative, the final formulation is created by backdiluting the phosphate process intermediate into buffer to a final desired concentration, e.g., a low concentration such as 20 mg/mL. Polysorbate is typically added during the final dilution step.

In one embodiment, the VLA-4 binding antibody formulation is produced in a histidine formulation, as described above, except that the phosphate process intermediate undergoes at least a second UF/DF process, and optionally, at least one additional UF process, into a histidine formulation buffer as described herein, to a final desired concentration, such as between about 75 mg/mL and 190 mg/mL, e.g., about 75 mg/mL to about 190 mg/mL, e.g., 75 mg/mL, 100 mg/mL, 125 mg/mL, 135 mg/mL, 150 mg/mL, 165 mg/mL, 180 mg/mL, 190 mg/mL. In one alternative, the antibody formulation in histidine buffer is brought to a final concentration greater than a desired concentration. Then the final formulation is created by backdiluting into histidine formulation buffer to a desired protein concentration. Polysorbate is typically added during the final dilution step.

In another embodiment, the antibody formulation is produced in a phosphate formulation, as described above, except that the phosphate process intermediate undergoes at least a second UF/DF process, and optionally, at least a one additional UF process, into a phosphate formulation buffer as described herein, to a final desired concentration, such as between about 75 mg/mL and 190 mg/mL, e.g., about 75 mg/mL to about 190 mg/mL, e.g., 75 mg/mL, 100 mg/mL, 125 mg/mL, 135 mg/mL, 150 mg/mL, 165 mg/mL, 180 mg/mL, 190 mg/mL. In one alternative, the antibody formulation in phosphate buffer is brought to a final concentration greater than the desired concentration, and the final formulation is created by backdiluting into phosphate buffer to the desired concentration. Polysorbate is typically added during the final dilution step.

In another embodiment, the VLA-4 binding antibody formulation is produced in a phosphate formulation, as described above, except that a commercial UF/DF process for the phosphate formulation is followed, and polysorbate added, to produce a VLA-4 binding antibody formulation at a desired final concentration, such as between about 75 mg/mL and 190 mg/mL, e.g., about 75 mg/mL to about 190 mg/mL, e.g., 75 mg/mL, 100 mg/mL, 125 mg/mL, 135 mg/mL, 150 mg/mL, 165 mg/mL, 180 mg/mL, 190 mg/mL. In one alternative, the antibody formulation in phosphate buffer is brought to a final concentration greater than the desired concentration, and then the final formulation is created by backdiluting into phosphate formulation buffer to the desired protein concentration. Polysorbate is typically added during the final dilution process.

TABLE 1

Methods of making antibody formulations.

| IV Formulation Process | High Concentration Clinical Process (Histidine Formulation) | High Concentration Clinical Process (Phosphate Formulation) | High Concentration Commercial Phosphate Process |
| --- | --- | --- | --- |
| 15,000 L Cell Culture ↓ Harvest and Clarification ↓ Purification (Chromatography, Viral Inactivation, and Viral Filtration) ↓ UF/DF into phosphate process intermediate N/A | 15,000 L Cell Culture ↓ Harvest and Clarification ↓ Purification (Chromatography, Viral Inactivation, and Viral Filtration) ↓ UF/DF #1 into phosphate process intermediate. If needed, storage at 2-8° C. UF/DF #2, and UF#3 into the histidine buffer at 150 mg/mL | 15,000 L Cell Culture ↓ Harvest and Clarification ↓ Purification (Chromatography, Viral Inactivation, and Viral Filtration) ↓ UF/DF #1 into phosphate process intermediate. If needed, storage at 2-8° C. UF/DF #2, and UF #3 into the phosphate Formulation buffer at 150 mg/mL | 15,000 L Cell Culture ↓ Harvest and Clarification ↓ Purification (Chromatography, Viral Inactivation, and Viral Filtration) ↓ Commercial UF/DF process for phosphate formulation at 150 mg/mL N/A |
| Final Formulation (polysorbate addition) and filling the Drug Substance | Final Formulation (polysorbate addition) and filling the Drug Substance | Final Formulation (polysorbate addition) and filling the Drug Substance | Final Formulation (polysorbate addition) and filling the Drug Substance |

The UF/DF processes of Table 1 (e.g., UF/DF #1, UF/DF#2) are typically tangential flow processes that use, e.g., flat sheet or spiral wound ultra-filtration cassettes (with, e.g., 10 kD or 30 kD pore sizes) to concentrate and diafilter the antibody. Such processes are suitable for concentrating the product to 0 to 100 g/L, e.g., 30 g/L, 50 g/L, 80 g/L. The UF processes of Table 1 (e.g., UF #3) typically use open-channel flat-sheet cassettes, which are suitable for concentrating the product to, e.g., 0 to 300 g/L or greater, such as to 150 g/L, 200 g/L, 210 g/L, 220 g/L, 230 g/L, or 240 g/L.

The commercial UF/DF process of Table 1 typically uses a first UF/DF operation to diafilter the product into a formulation buffer and concentrate the product to about 5 g/L to 40 g/L (e.g., about 10 g/L, about 20 g/L, about 30 g/L). A second UF operation is typically performed to further concentrate the product to about 135 g/L to about 185 g/L (e.g., about 140 g/L, 150 g/L, 165 g/L).

Any of the VLA-4 binding antibody formulations described herein can be packaged in aseptic vials as described in, e.g., U.S. Published Application 2005/0053598, which is incorporated herein by reference. For example, the formulations can be packaged in, e.g., 3.0, 5.0 or 20 mL fill vials. Filled drug product is stored under refrigeration at about 2-8° C.

In one embodiment, the final formulation is packaged as a liquid in a 3.0 mL fill vial with an extractable minimum volume of 1 mL. For example, the fill vial can include about 1.1 mL to about 1.5 mL (e.g., about 1.1 mL, about 1.2 mL, about 1.3 mL, about 1.4 mL) of antibody formulation. In another embodiment, that antibody formulation is packaged in a pre-filled syringe, in an amount such that 1 mL of solution is injected into a patient upon use, and the 1 mL solution delivers the desired amount of antibody, e.g., 135 mg to 165 mg natalizumab, e.g., 150 mg natalizumab.

Natalizumab and Other VLA-4 Binding Antibodies

Antibodies suitable for a highly concentrated VLA-4 binding antibody formulation described herein include natalizumab, an α4 integrin binding antibody. Natalizumab (USAN name) has the antibody code number AN100226, and is also called "TYSABRI™" The amino acid sequence of the light chain and heavy chain of natalizumab prior to any in vivo modifications (e.g., clipping of amino acids) is shown in Table 1-1 and Table 1-2.

TABLE 1-1

Sequence of Natalizumab Light Chain (SEQ ID NO: 1)

```
              10          20          30          40          50
  1 DIQMTQSPSS LSASVGDRVT ITCKTSQDIN KYMAWYQQTP GKAPRLLIHY

51 TSALQPGIPS RFSGSGSGRD YTFTISSLQP EDIATYYCLQ YDNLWTFGQG

101 TKVEIKRTVA APSVFIFPPS DEQLKSGTAS VVCLLNNFYP REAKVQWKVD

151 NALQSGNSQE SVTEQDSKDS TYSLSSTLTL SKADYEKHKV YACEVTHQGL

201 SSPVTKSFNR GEC
```

TABLE 1-2

Sequence of Natalizumab Heavy Chain (SEQ ID NO: 2)

```
              10          20          30          40          50
    Q¹VQLVQSGAE VKKPGASVKV SCKASGFNIK DTYIHWVRQA PGQRLEWMGR

IDPANGYTKY DPKFQGRVTI TADTSASTAY MELSSLRSED TAVYYCAREG

YYGNYGVYAM DYWGQGTLVT VSSASTKGPS VFPLAPCSRS TSESTAALGC

LVKDYFPEPV TVSWNSGALT SGVHTFPAVL QSSGLYSLSS VVTVPSSSLG

TKTYTCNVDH KPSNTKVDKR VESKYGPPCP SCPAPEFLGG PSVFLFPPKP

KDTLMISRTP EVTCVVVDVS QEDPEVQFNW YVDGVEVHNA KTKPREEQFN

STYRVVSVLT VLHQDWLNGK EYKCKVSNKG LPSSIEKTIS KAKGQPREPQ

VYTLPPSQEE MTKNQVSLTC LVKGFYPSDI AVEWESNGQP ENNYKTTPPV

LDSDGSFFLY SRLTVDKSRW QEGNVFSCSV MHEALHNHYT QKSLSLSLGK²
```

[1]Glutamine cyclized to pyroGlutamic Acid
[2]Lysine is removed posttranslationally Natalizumab inhibits the migration of leukocytes from the blood to the central nervous system. Natalizumab binds to VLA-4 (also called α4β1) on the surface of activated T-cells and other mononuclear leukocytes. It can disrupt adhesion between the T-cell and endothelial cells, and thus prevent migration of mononuclear leukocytes across the endothelium and into the parenchyma. As a result, the levels of proinflammatory cytokines can also be reduced.

Natalizumab can decrease the number of brain lesions and clinical relapses in patients with relapse remitting multiple sclerosis and relapsing secondary-progressive multiple sclerosis.

Natalizumab and related VLA-4 binding antibodies are described, e.g., in U.S. Pat. No. 5,840,299. Monoclonal antibodies 21.6 and HP1/2 are exemplary murine monoclonal antibodies that bind VLA-4. Natalizumab is a humanized version of murine monoclonal antibody 21.6 (see, e.g., U.S. Pat. No. 5,840,299). A humanized version of HP1/2 has also been described (see, e.g., U.S. Pat. No. 6,602,503). Several additional VLA-4 binding monoclonal antibodies, such as HP2/1, HP2/4, L25 and P4C2, are described, e.g., in U.S. Pat. No. 6,602,503; Sanchez-Madrid et al., 1986 *Eur. J. Immunol.*, 16:1343-1349; Hemler et al., 1987 *J. Biol. Chem.* 2:11478-11485; Issekutz and Wykretowicz, 1991, *J. Immunol.*, 147: 109 (TA-2 mab); Pulido et al., 1991 *J. Biol. Chem.*, 266:10241-10245; and U.S. Pat. No. 5,888,507).

Some VLA-4 binding antibodies recognize epitopes of the a4 subunit that are involved in binding to a cognate ligand, e.g., VCAM-1 or fibronectin. Many such antibodies inhibit binding of VLA-4 to cognate ligands (e.g., VCAM-1 and fibronectin).

Some useful VLA-4 binding antibodies can interact with VLA-4 on cells, e.g., lymphocytes, but do not cause cell aggregation. However, other VLA-4 binding antibodies have been observed to cause such aggregation. HP1/2 does not cause cell aggregation. The HP1/2 monoclonal antibody (Sanchez-Madrid et al., 1986) has an extremely high potency, blocks VLA-4 interaction with both VCAM1 and fibronectin, and has the specificity for epitope B on VLA-4. This antibody and other B epitope-specific antibodies (such as B1 or B2 epitope binding antibodies; Pulido et al., 1991, supra) represent one class of VLA-4 binding antibodies that can be used in the formulations and methods described herein.

An exemplary VLA-4 binding antibody has one or more CDRs, e.g., all three HC CDRs and/or all three LC CDRs of a particular antibody disclosed herein, or CDRs that are, in sum, at least 80, 85, 90, 92, 94, 95, 96, 97, 98, 99% identical to such an antibody, e.g., natalizumab. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 70, 80, 85, 90, 92, 95, 97, 98, 99, or 100% identical to the amino acid sequence of the HC and/or LC variable domain of an antibody described herein, e.g., natalizumab. The amino acid sequence of the HC and/or LC variable domain sequence can differ by at least one amino acid, but no more than ten, eight, six, five, four, three, or two amino acids from the corresponding sequence of an antibody described herein, e.g., natalizumab. For example, the differences may be primarily or entirely in the framework regions.

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein. In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of an antibody described herein. In one embodiment, one or more heavy or light chain framework regions (e.g., HC FR1, FR2, and FR3) are at least 70, 80, 85, 90, 95, 96, 97, 98, or 100% identical to the sequence of corresponding framework regions from a human germline antibody.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

As used herein, the term "hybridizes under high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Administration

The highly concentrated VLA-4 binding antibody formulations described herein can be administered to a subject, e.g., a human subject, by a variety of methods, including subcutaneous, intramuscular and intravenous administration. Typically, administration is by subcutaneous or intramuscular injection.

The formulation can be administered as a fixed dose, or in a mg/kg dose. Typically the administration is in a fixed dose. For example, the formulation is administered at a fixed unit dose of between 75 mg and 500 mg (e.g., 100 mg, 150 mg, 200 mg, 250 mg, 300 mg, 350 mg, 400 mg, 450 mg) every 4 weeks (e.g., monthly), or between 50 mg and 250 mg (e.g., 75 mg, 100 mg, 150 mg, 200 mg) every two weeks, or between 25 mg and 150 mg (e.g., 50 mg, 75 mg, 100 mg, 125 mg) once a week. The formulation can also be administered in a bolus at a dose of between 1 and 8 mg/kg, e.g., about 6.0, 4.0, 3.0, 2.0, 1.0 mg/kg. Modified dose ranges include a dose that is less than 500, 400, 300, 250, 200, 150 or 100 mg/subject, typically for administration every fourth week or once a month. The VLA-4 binding antibody can be administered, for example, every three to five weeks, e.g., every fourth week, or monthly.

Dosage regimens can be adjusted to provide the desired response, e.g., a therapeutic response. The dose can also be chosen to reduce or avoid production of antibodies against the VLA-4 binding antibody, to achieve greater than 40, 50, 70, 75, or 80% saturation of the α4 subunit, to achieve to less than 80%, 70%, 60%, 50%, or 40% saturation of the α4 subunit, or to prevent an increase the level of circulating white blood cells.

In certain embodiments, the active agent can be prepared with a carrier that will protect the antibody against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

Dosage regimens can be adjusted to provide the desired response, e.g., a therapeutic response. A "therapeutic response" is an improvement in a condition, symptom, or parameter associated with a disorder, to either a statistically significant degree or to a degree detectable to one skilled in the art.

Dosage unit form or "fixed dose" as used herein refers to physically discrete units suited as unitary dosages for the subjects to be treated; each unit contains a predetermined quantity of active antibody calculated to produce the desired therapeutic effect in association with the required pharmaceutical carrier and optionally in association with the other agent.

A pharmaceutical composition may include a "therapeutically effective amount" of a VLA-4-binding antibody, e.g. natalizumab, described herein. Such effective amounts can be determined based on the effect of the administered agent, or the combinatorial effect of an agent and secondary agent if more than one agent is used. A therapeutically effective amount of an agent may also vary according to factors such as the disease state, age, sex, and weight of the individual, and the ability of the antibody to elicit a desired response in the individual, e.g., amelioration of at least one disorder parameter, e.g., a multiple sclerosis parameter, or amelioration of at least one symptom of the disorder, e.g., multiple sclerosis. A therapeutically effective amount is also one in which any toxic or detrimental effects of the composition are outweighed by the therapeutically beneficial effects.

Devices and Kits

Formulations having a high concentration of a VLA-4-binding antibody (e.g., natalizumab) can be administered with a medical device. The device can be designed with or have features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include a VLA-4-binding antibody (e.g., natalizumab), and can be configured to deliver one or more unit doses of the agent.

For example, the pharmaceutical composition can be administered with a transcutaneous delivery device, such as a syringe, including a hypodermic or multichamber syringe. In one embodiment, the device is a prefilled syringe with attached or integral needle. In other embodiments, the device is a prefilled syringe not having a needle attached. The needle can be packaged with the prefilled syringe. In one embodiment, the device is an auto-injection device, e.g., an auto-injector syringe. In another embodiment the injection device is a pen-injector. In yet another embodiment, the syringe is a staked needle syringe, luer lock syringe, or luer slip syringe. Other suitable delivery devices include stents, catheters, microneedles, and implantable controlled release devices. The composition can be administered intravenously with standard IV equipment, including, e.g., IV tubings, with or without in-line filters. In certain embodiments, the device will be a syringe for use in SC or IM administration.

Pharmaceutical compositions can be administered with medical devices. For example, pharmaceutical compositions can be administered with a needleless hypodermic injection device, such as the devices disclosed in U.S. Pat. No. 5,399,163, 5,383,851, 5,312,335, 5,064,413, 4,941,880, 4,790,824, or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. The therapeutic composition can also be in the form of a biodegradable or nonbiodegradable sustained release formulation for subcutaneous or intramuscular administration. See, e.g., U.S. Pat. Nos. 3,773,919 and 4,767,628 and PCT Application No. WO 94/15587. Continuous administration can also be achieved using an implantable or external pump. The administration can also be conducted intermittently, e.g., single daily injection, or continuously at a low dose, e.g., sustained release formulation. The delivery device can be modified to be optimally suited for administration of VLA-4 binding antibody. For example, a syringe can be siliconized to an extent that is optimal for storage and delivery of anti-VLA-4 antibody. Of course, many other such implants, delivery systems, and modules are also known.

The invention also features a device for administering a first and second agent. The device can include, e.g., one or more housings for storing pharmaceutical preparations, and can be configured to deliver unit doses of the first and second agent. The first and second agents can be stored in the same or separate compartments. For example, the device can combine the agents prior to administration. It is also possible to use different devices to administer the first and second agent.

A VLA-4-binding antibody (e.g., natalizumab) can be provided in a kit. In one embodiment, the kit includes (a) a container that contains a composition that includes a high concentration of VLA-4-binding antibody, optionally (b) a container that contains a composition that includes a second agent and optionally (c) informational material. The informational material can be descriptive, instructional, marketing or other material that relates to the methods described herein and/or the use of the agents for therapeutic benefit. In one embodiment, the kit also includes a second agent. For example, the kit includes a first container that contains a composition that includes the VLA-4-binding antibody, and a second container that includes the second agent. In one embodiment, the kit includes one or more single-use syringes pre-filled with a high concentration liquid antibody formulation described herein.

The informational material of the kits is not limited in its form. In one embodiment, the informational material can include information about production of the antibody, concentration, date of expiration, batch or production site information, and so forth. In one embodiment, the informational material relates to methods of administering the VLA-4-binding antibody (e.g., natalizumab), e.g., in a suitable dose, dosage form, or mode of administration (e.g., a dose, dosage form, or mode of administration described herein), to treat a subject who has an inflammatory disease (e.g., MS), or who is at risk for experiencing an episode associated with an inflammatory disease. The information can be provided in a variety of formats, including printed text, computer readable material, video recording, or audio recording, or information that provides a link or address to substantive material.

In addition to the agent, the composition in the kit can include other ingredients, such as a solvent or buffer, a stabilizer, or a preservative. The agent can be provided in any form, e.g., liquid, dried or lyophilized form, and in substantially pure and/or sterile form. When the agents are provided in a liquid solution, the liquid solution is, for example, an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the VLA-4-binding antibody (e.g., natalizumab) and the second agent, e.g., in a desired ratio. For example, the kit includes a plurality of syringes, ampoules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Multiple Sclerosis

Formulations having highly concentrated VLA-4 binding antibody suitable for SC or IM administration are useful for the treatment of inflammatory diseases, such as multiple sclerosis (MS). Multiple sclerosis is a central nervous system disease that is characterized by inflammation and loss of myelin sheaths.

Patients having MS may be identified by criteria establishing a diagnosis of clinically definite MS as defined by the workshop on the diagnosis of MS (Poser et al., *Ann. Neurol.* 13:227, 1983). Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. (McDonald et al., 2001, *Recommended diagnostic criteria for multiple sclerosis: guidelines from the International Panel on the Diagnosis of Multiple Sclerosis*, Ann Neurol 50:121-127). The McDonald criteria include the use of MRI evidence of CNS impairment over time to be used in diagnosis of MS, in the absence of multiple clinical attacks. Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging). The EDSS is a means to grade clinical impairment due to MS (Kurtzke, *Neurology* 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step indicates an effective treatment (Kurtzke, *Ann. Neurol.* 36:573-79, 1994).

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al., *Neurology* 34:1368, 1984). An annual exacerbation rate and proportion of exacerbation-free patients are determined.

Therapy can be deemed to be effective if there is a statistically significant difference in the rate or proportion of exacerbation-free or relapse-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, or 20 months is particularly noteworthy.

Efficacy of administering a first agent and, optionally, a second agent, can also be evaluated based on one or more of the following criteria: frequency of MBP reactive T cells determined by limiting dilution, proliferation response of MBP reactive T cell lines and clones, cytokine profiles of T cell lines and clones to MBP established from patients. Efficacy is indicated by decrease in frequency of reactive cells, a reduction in thymidine incorporation with altered peptide compared to native, and a reduction in TNF and IFN-α.

Clinical measurements include the relapse rate in one and two-year intervals, and a change in EDSS, including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images.

MRI can be used to measure active lesions using gadolinium-DTPA-enhanced imaging (McDonald et al. *Ann. Neurol.* 36:14, 1994) or the location and extent of lesions using $T_2$—weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of MS lesions can be determined by radiologists. Areas of lesions can be outlined and summed slice by slice for total lesion area. Three analyses may be done: evidence of new lesions, rate of appearance of active lesions, percentage change in lesion area (Paty et al., *Neurology* 43:665, 1993). Improvement due to therapy can be established by a statistically significant improvement in an individual patient compared to baseline or in a treated group versus a placebo group.

Exemplary symptoms associated with multiple sclerosis, which can be treated with the methods described herein, include: optic neuritis, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, uhthoff's symptom, gastroesophageal reflux, and sleeping disorders.

Each case of MS displays one of several patterns of presentation and subsequent course. Most commonly, MS first manifests itself as a series of attacks followed by complete or partial remissions as symptoms mysteriously lessen, only to return later after a period of stability. This is called relapsing-remitting (RR) MS. Primary-progressive (PP) MS is characterized by a gradual clinical decline with no distinct remissions, although there may be temporary plateaus or minor relief from symptoms. Secondary-progressive (SP) MS begins with a relapsing-remitting course followed by a later primary-progressive course. Rarely, patients may have a progressive-relapsing (PR) course in which the disease takes a progressive path punctuated by acute attacks. PP, SP, and PR are sometimes lumped together and called chronic progressive MS.

A few patients experience malignant MS, defined as a swift and relentless decline resulting in significant disability or even death shortly after disease onset. This decline may be arrested or decelerated by administration of a combination therapy described herein.

In addition to or prior to human studies, an animal model can be used to evaluate the efficacy of using the two agents. An exemplary animal model for multiple sclerosis is the experimental autoimmune encephalitis (EAE) mouse model, e.g., as described in (Tuohy et al. (*J. Immunol.* (1988) 141: 1126-1130), Sobel et al. (*J. Immunol.* (1984) 132: 2393-2401), and Traugott (*Cell Immunol.* (1989) 119: 114-129). Mice can be administered a first and second agent described herein prior to EAE induction. Then the mice are evaluated for characteristic criteria to determine the efficacy of using the two agents in the model.

Other Disorders

The formulations and methods described herein can also be used to treat other inflammatory, immune, or autoimmune disorders, e.g., inflammation of the central nervous system (e.g., in addition to multiple sclerosis, meningitis, neuromyelitis optica, neurosarcoidosis, CNS vasculitis, encephalitis, and transverse myelitis), tissue or organ graft rejection or graft-versus-host disease, acute CNS injury, e.g., stroke or spinal cord injury; chronic renal disease; allergy, e.g., allergic asthma; type 1 diabetes; inflammatory bowel disorders, e.g., Crohn's disease, ulcerative colitis; myasthenia gravis; fibromyalgia; arthritic disorders, e.g., rheumatoid arthritis, psoriatic arthritis; inflammatory/immune skin disorders, e.g., psoriasis, vitiligo, dermatitis, lichen planus; systemic lupus erythematosus; Sjogren's Syndrome; hematological cancers, e.g., multiple myeloma, leukemia, lymphoma; solid cancers, e.g., sarcomas or carcinomas, e.g., of the lung, breast, prostate, brain; and fibrotic disorders, e.g., pulmonary fibrosis, myelofibrosis, liver cirrhosis, mesangial proliferative glomerulonephritis, crescentic glomerulonephritis, diabetic nephropathy, and renal interstitial fibrosis.

For example, a formulation containing a high concentration of VLA-4 binding antibody, (e.g., natalizumab) can be administered subcutaneously or intramuscularly to treat these and other inflammatory, immune, or autoimmune disorders.

Antibody Generation

Antibodies that bind to VLA-4 can be generated by immunization, e.g., using an animal, or by in vitro methods such as phage display. All or part of VLA-4 can be used as an immunogen. For example, the extracellular region of the α4 subunit can be used as an immunogen. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XenoMouse™, Green et al. *Nature Genetics* 7:13-21 (1994), U.S. 2003-0070185, U.S. Pat. No. 5,789,650, and WO 96/34096.

Non-human antibodies to VLA-4 can also be produced, e.g., in a rodent. The non-human antibody can be humanized, e.g., as described in U.S. Pat. No. 6,602,503, EP 239 400, U.S. Pat. No. 5,693,761, and U.S. Pat. No. 6,407,213.

EP 239 400 (Winter et al.) describes altering antibodies by substitution (within a given variable region) of their complementarity determining regions (CDRs) for one species with those from another. CDR-substituted antibodies can be less likely to elicit an immune response in humans compared to true chimeric antibodies because the CDR-substituted antibodies contain considerably less non-human components. (Riechmann et al., 1988, *Nature* 332, 323-327; Verhoeyen et al., 1988, *Science* 239, 1534-1536). Typically, CDRs of a murine antibody substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody.

Queen et al., 1989 and WO 90/07861 have described a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, *Biotechnology* 9, 266-271, utilize, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from X-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more (such as at least five, ten, twelve, or all) of the following positions: (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

Fully human monoclonal antibodies that bind to VLA-4 can be produced, e.g., using in vitro-primed human splenocytes, as described by Boerner et al., 1991, *J. Immunol.*, 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798,230. Large nonimmunized human phage display libraries may also be used to isolate high affinity antibodies that can be developed as human therapeutics using standard phage technology (see, e.g., Vaughan et al, 1996; Hoogenboom et al. (1998) *Immunotechnology* 4:1-20; and Hoogenboom et al. (2000) *Immunol Today* 2:371-8; U.S. 2003-0232333).

Antibody Production

Antibodies can be produced in prokaryotic and eukaryotic cells. In one embodiment, the antibodies (e.g., scFvs) are expressed in a yeast cell such as *Pichia* (see, e.g., Powers et al. (2001) *J Immunol Methods*. 251:123-35), *Hanseula*, or *Saccharomyces*.

In one embodiment, antibodies, particularly full length antibodies, e.g., IgGs, are produced in mammalian cells. Exemplary mammalian host cells for recombinant expression include Chinese Hamster Ovary (CHO cells) (including dhfr– CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NSO myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). Exemplary selectable marker genes include the dihydrofolate reductase (DHFR) gene (for use in dhfr⁻ host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G. For example, purified VLA-4-binding antibodies, e.g. natalizumab, can be concentrated to about 100 mg/mL to about 200 mg/mL using standard protein concentration techniques.

Antibodies may also include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some antibodies that include an Fc domain, the antibody production system may be designed to synthesize antibodies in which the Fc region is glycosylated. For example, the Fc domain of IgG molecules is glycosylated at asparagine 297 in the CH2 domain. This asparagine is the site for modification with biantennary-type oligosaccharides. This glycosylation participates in effector functions mediated by Fcγ receptors and complement C1q (Burton and Woof (1992) *Adv. Immunol.* 51:1-84; Jefferis et al. (1998) *Immunol. Rev.* 163:59-76). The Fc domain can be produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the antibody of interest, e.g., an antibody described herein. The antibody can be purified from the milk, or for some applications, used directly.

Antibodies can be modified, e.g., with a moiety that improves its stabilization and/or retention in circulation, e.g., in blood, serum, lymph, bronchoalveolar lavage, or other tissues, e.g., by at least 1.5, 2, 5, 10, or 50 fold.

For example, a VLA-4 binding antibody can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 daltons (or about 1,000 to about 15,000, and 2,000 to about 12,500) can be used.

For example, a VLA-4 binding antibody can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Exemplary Second Agents

In some cases, the formulations described herein, e.g., formulations containing a high concentration of VLA-4 binding antibody suitable for SC or IM administration, include a second agent, or are administered in combination with a formulation containing a second agent.

In one implementation, the VLA-4 binding antibody and second agent is provided as a co-formulation, and the co-formulation is administered to the subject. It is further possible, e.g., at least 24 hours before or after administering the co-formulation, to administer separately one dose of the highly concentrated antibody formulation and then one dose of a formulation containing the second agent. In another implementation, the antibody and the second agent are provided as separate formulations, and the step of administering includes sequentially administering the antibody and the second agent. The sequential administrations can be provided on the same day (e.g., within one hour of one another or at least 3, 6, or 12 hours apart) or on different days.

Generally, the antibody and the second agent are each administered as a plurality of doses separated in time. The antibody and the second agent are generally each administered according to a regimen. The regimen for one or both may have a regular periodicity. The regimen for the antibody can have a different periodicity from the regimen for the second agent, e.g., one can be administered more frequently than the other. In one implementation, one of the antibody and the second agent is administered once weekly and the other once monthly. In another implementation, one of the antibody and the second agent is administered continuously, e.g., over a period of more than 30 minutes but less than 1, 2, 4, or 12 hours, and the other is administered as a bolus. The antibody and the second agent can be administered by any appropriate method, e.g., subcutaneously, intramuscularly, or intravenously.

In some embodiments, each of the antibody and the second agent is administered at the same dose as each is prescribed for monotherapy. In other embodiments, the antibody is administered at a dosage that is equal to or less than an amount required for efficacy if administered alone. Likewise, the second agent can be administered at a dosage that is equal to or less than an amount required for efficacy if administered alone.

Non-limiting examples of second agents for treating multiple sclerosis in combination with a VLA-4 binding antibody include:

interferons, e.g., human interferon beta-1a (e.g., AVONEX® or Rebif®)) and interferon beta-1b (BE-TASERON™; human interferon beta substituted at position 17; Berlex/Chiron);

glatiramer acetate (also termed Copolymer 1, Cop-1; COPAXONE™; Teva Pharmaceutical Industries, Inc.);

Rituxan® (rituximab) or another anti-CD20 antibody, e.g., one that competes with or binds an overlapping epitope with rituximab;

mixtoxantrone (NOVANTRONE®, Lederle);

a chemotherapeutic, e.g., clabribine (LEUSTATIN®), azathioprine (IMURAN®), cyclophosphamide (CYTOXAN®), cyclosporine-A, methotrexate, 4-aminopyridine, and tizanidine;

a corticosteroid, e.g., methylprednisolone (MEDRONE®, Pfizer), prednisone;

an immunoglobulin, e.g., Rituxan® (rituximab); CTLA4 Ig; alemtuzumab (MabCAMPATH®) or daclizumab (an antibody that binds CD25);

statins;

TNF antagonists.

Glatiramer acetate is a protein formed of a random chain of amino acids—glutamic acid, lysine, alanine and tyrosine (hence GLATiramer). It can be synthesized in solution from these amino acids a ratio of approximately 5 parts alanine to 3 of lysine, 1.5 of glutamic acid and 1 of tyrosine using N-carboxyamino acid anhydrides.

Additional second agents include antibodies or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. Still other exemplary second agents include antibodies to cell surface molecules such as CD2, CD3, CD4, CD8, CD25, CD28, CD30, CD40, CD45, CD69, CD80, CD86, CD90 or their ligands. For example, daclizubmab is an anti-CD25 antibody that may ameliorate multiple sclerosis.

Still other exemplary antibodies include antibodies that provide an activity of an agent described herein, e.g., an antibody that engages an interferon receptor, e.g., an interferon beta receptor. Typically, in implementations in which the second agent includes an antibody, it binds to a target protein other tha VLA-4 or other than α4 integrin, or at least an epitope on VLA-4 other than one recognized by the first agent.

Still other additional exemplary second agents include: FK506, rapamycin, mycophenolate mofetil, leflunomide, non-steroidal anti-inflammatory drugs (NSAIDs), for example, phosphodiesterase inhibitors, adenosine agonists, antithrombotic agents, complement inhibitors, adrenergic agents, agents that interfere with signaling by proinflammatory cytokines as described herein, IL-Iβ converting enzyme inhibitors (e.g., V×740), anti-P7s, PSGL, TACE inhibitors, T-cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, anti-inflammatory cytokines (e.g. IL-4, IL-10, IL-13 and TGF).

In some embodiments, a second agent may be used to treat one or more symptoms or side effects of MS. Such agents include, e.g., amantadine, baclofen, papaverine, meclizine, hydroxyzine, sulfamethoxazole, ciprofloxacin, docusate, pemoline, dantrolene, desmopressin, dexamethasone, tolterodine, phenytoin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline. Many second agents that are small molecules have a molecular weight between 150 and 5000 Daltons.

Examples of TNF antagonists include chimeric, humanized, human or in vitro generated antibodies (or antigen-binding fragments thereof) to TNF (e.g., human TNF α), such as D2E7, (human TNFα antibody, U.S. Pat. No. 6,258,562; BASF), CDP-571/CDP-870/BAY-10-3356 (humanized anti-TNFα antibody; Celltech/Pharmacia), cA2 (chimeric anti-TNFα antibody; REMICADE™, Centocor); anti-TNF antibody fragments (e.g., CPD870); soluble fragments of the TNF receptors, e.g., p55 or p75 human TNF receptors or derivatives thereof, e.g., 75 kDTNFR-IgG (75 kD TNF receptor-IgG fusion protein, ENBREL™; Immunex; see e.g., Arthritis & Rheumatism (1994) Vol. 37, 5295; J. Invest. Med. (1996) Vol. 44, 235A), p55 kdTNFR-IgG (55 kD TNF receptor-IgG fusion protein (LENERCEPT™)); enzyme antagonists, e.g., TNFα converting enzyme (TACE) inhibitors (e.g., an alpha-sulfonyl hydroxamic acid derivative, WO 01/55112, and N-hydroxyformamide TACE inhibitor GW 3333, -005, or -022); and TNF-bp/s-TNFR (soluble TNF binding protein; see e.g., Arthritis & Rheumatism (1996) Vol. 39, No. 9 (supplement), S284; Amer. J. Physiol.—Heart and Circulatory Physiology (1995) Vol. 268, pp. 37-42).

In addition to a second agent, it is also possible to deliver still other agents to the subject. However, in some embodiments, no protein or no biologic, other than the VLA-4 binding antibody and second agent, are administered to the subject as a pharmaceutical composition. The VLA-4 binding antibody and the second agent may be the only agents that are delivered by injection. In embodiments in which the VLA-4 binding antibody and the second agent are recombinant proteins, the VLA-4 binding antibody and second agent may be the only recombinant agents administered to the subject, or at least the only recombinant agents that modulate immune or inflammatory responses. In still other embodiments, the VLA-4 binding antibody alone is the only recombinant agent or the only biologic administered to the subject.

All references and publications included herein are incorporated by reference. The following examples are not intended to be limiting.

EXAMPLES

Example 1

Summary of Development of Intravenous Formulation: Storage and Structural Stability Experiments were performed to determine the storage stability of a formulation of natalizumab containing 20 mg/mL natalizumab in 10 mM phosphate, 140 mM sodium chloride, 0.02% polysorbate 80, pH 6. Rates of stability change during storage of the formulation were calculated for different storage condition data sets (2-8° C. for 24 months; 25° C. for 12 months; 40° C. for 3 months). The following parameters were used to assess the rates of stability change compared to the initial time point: percentage of aggregation, percentage of oxidation of amino acid residue Methionine 255, percentage of half-antibody present, percentage of H+L, percentage of fragmentation, percentage of sialylation, and percentage of isoforms with a lower isoelectric point (pI). The results of storage stability formulation developmental trials are shown in Table 2. These results also provide a baseline for stability studies of formulations containing higher antibody concentrations.

TABLE 2

20 mg/mL formulation: storage stability.

| Attribute | Effect of Formulation Condition on Degradant | Change during storage | Rate of Change During Storage | | |
|---|---|---|---|---|---|
| | | | 2-8° C.[1] | 25° C.[2] | 40° C.[3] |
| % Aggregation | ~pH 6 optimum | Increase | N/C | ~0.1% per year | ~0.3% per month |
| % Met255 oxidation | Optimize by minimizing peroxide levels | Increase | N/C | N/C | ~0.4-1% per month |
| % Half-antibody | ~pH 5-6 optimum, excipient dependent | Increase | N/C | N/C | ~1%/month |
| % H + L | ~pH 5-6.5 optimum | Increase | N/C | N/C | ~1.5%/month |
| % Fragmentation | ~pH 5-6.5 optimum | Decrease | N/C | N/C | ~1%/month |
| % Sialylation | ~pH 5-6 optimum (predicted) | Decrease | N/C | N/C | N/D |
| % Lower pI isoforms | ~pH 5 optimum | Increase | ~1%/year | ~1.8%/month | ~14%/month |

[1]Rate calculated using 24 months real time data.
[2]Rate calculated using 12 month data set.
[3]Rate calculated using 3 month data set.
N/C—No Change, N/D—Not Determined.

Various biophysical techniques were used to assess the structural stability of the 20 mg/mL natalizumab formulation, including monitoring protein secondary structure through differential scanning calorimetry (DSC), monitoring the environment of tryptophan residues through tryptophan fluorescence with a fluorescent spectrophotometer, monitoring the tertiary structure of the IgG fold via circular dichroism in the far UV, and monitoring the environment of aromatic residues via UV and visible spectrophotometry.

Structural stability of the 20 mg/mL formulation was optimized, in part, by monitoring the $T_m$ (midpoint of thermal melting curve) during thermal melting experiments in a differential scanning calorimeter (Microcal, Amherst, Mass.). Excess enthalpy needed to melt the protein compared to buffer control was monitored and data were analyzed by computer. Tryptophan fluorescence, known to be sensitive to structural stability, was monitored by UV spectrophotometry in increasing temperatures to optimize formulation conditions. Again, UV spectrophotometry was used in the far UV region to measure the IgG fold. Six peaks were monitored, and the second derivative of the UV-Vis spectrum 230-320 nm was calculated in order to follow the environment of the aromatic residues as a measure of structural stability in various formulations.

Results of structural studies conducted to assess the stability of natalizumab at 20 mg/mL are shown in Table 3. Additional studies have shown that natalizumab undergoes heterogeneous nucleation during pumping with piston pumps. No change in antibody quality was observed after multiple freeze/thaw cycling and the antibody was stable after prolonged 2-3 days agitation in vials (data shown in Example 2). Natalizumab undergoes aggregation, oxidation, and deamidation in the presence of intense light stress and is also sensitive to metal-catalyzed oxidation when stored in contact with stainless steel for long periods of time.

TABLE 3

20 mg/mL formulation: structural stability.

| Molecular Property | Technique | Optimum Formulation Condition |
|---|---|---|
| Secondary Structure | DSC | Optimum pH between 7 and 8 (based on $T_m$ at 68° C.) |
| Tryptophan Environment | Fluorescence | pH ~7 (based on highest onset Temp between pH 4-9) |
| IgG fold | Far UV CD | Monitoring 215-218 nm, maximum $T_m$ at pH 7 without salt |
| Aromatic Residue Environment | $2^{nd}$ Derivative of UV-Vis peaks | 6 peaks were monitored, maximum $T_m$ between pH 5 and 7 |

Example 2

Accelerated Stability Experiments of 150 mg/mL Formulations

To determine a formulation suitable for higher concentrations of natalizumab, which would be useful for subcutaneous or intramuscular administration in particular, accelerated stability experiments were performed with 150 mg/mL natalizumab in various formulations. Test formulations were subjected to agitation in Type I USP/EP glass vials for several days at ambient temperature (about 25° C.). Formulations used in aggregation studies were as follows. HCN=20 mM histidine, 240 mM glycine, pH 6. HOL=20 mM histidine, 240 mM glycerol, pH 6. PCN=20 mM phosphate, 240 mM glycine, pH 6. PST=20 mM phosphate, 140 mM NaCl, pH 6. HOL and HCN formulations have an additional 0.04% (w/v) polysorbate 80 (w/v). PCN and PST formulations have an additional 0.02% (w/v) polysorbate 80, except when being tested as a variable for stability (Experiment 3 below). Size exclusion chromatography (SEC) was used to measure the percentage aggregation before and after the agitation.

Levels of soluble aggregates pre- and post-agitation are shown in FIG. 1. Percentage of soluble aggregates were measured by SEC, and the smallest change in percentage of soluble aggregates was observed in the HOL formulation (20 mM histidine, 240 mM glycerol, 0.04% (w/v) polysorbate 80, pH 6).

Accelerated stability tests were performed as described above were also monitored by UV absorbance to detect aggregates. A UV spectrophotometer was used to monitor the presence of aggregates pre- and post-agitation by measuring absorbance at 340 nm for solutions of natalizumab at a concentration of 150 mg/mL in HCN, HOL, PCN, and PST buffers as described above, in a UV/Vis spectrophotometer with a 1 cm path length.

Figure 2:
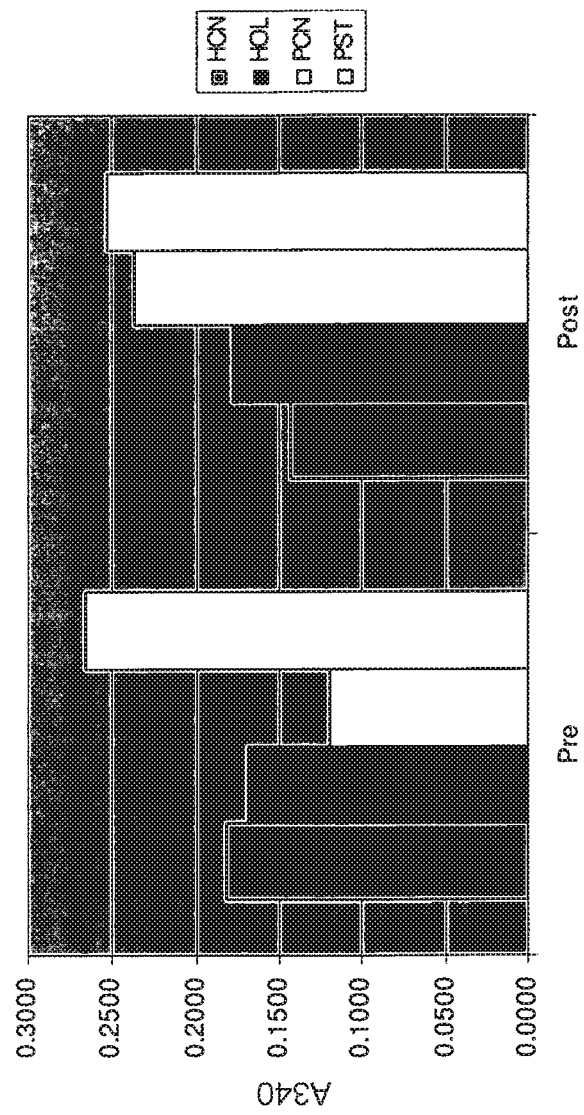
FIG. 2 shows the UV absorbance in solution at 340 nm pre- and post-agitation of natalizumab at a concentration of 150 mg/mL in formulations as described in FIG. 1.

The results of the UV absorbance study of aggregation of natalizumab (150 mg/mL) in various formulation pre- and post-agitation can be seen in FIG. 2. The histidine formulations (HOL and HCN) were most stable under these conditions, as evidenced by the lower absorbance at 340 nm, indicating less aggregation. Insoluble precipitates were observed in the phosphate formulations after storage for 1 month at 40° C., but were not observed in the histidine formulations.

Table 4 compares stability attributes of the 20 mg/mL and 150 mg/mL formulations. The results indicate that the 20 mg/mL and 150 mg/mL formulations are similarly stable.

TABLE 4

Stability attributes at 20 mg/mL and 150 mg/mL

| | Average Rate of Change, 5° C., per year | |
|---|---|---|
| Attribute | 20 mg/ml | 150 mg/mL |
| Aggregation by SEC | <0.5% | <0.5% |
| Acidic isoforms | ~1% | ~1% |
| Oxidation | <0.5% | <0.5% |
| Purity (% H + L) | <−0.5% | <−0.5% |
| Potency | No Change | No Change |

Example 3

Polysorbate-80 has a Solubilizing Effect on Natalizumab

The solubilizing effects of polysorbate-80 levels on natalizumab at 20 mg/mL and 150 mg/mL were investigated. Polysorbate-80 was added at various concentrations (w/v) to 20 mg/mL and 150 mg/mL natalizumab in HOL buffer. Accelerated stability testing was performed by agitating the materials as described above, for 8 weeks at 40° C. Percentage aggregation was measured by SEC as described in the Example above.

Figure 3:
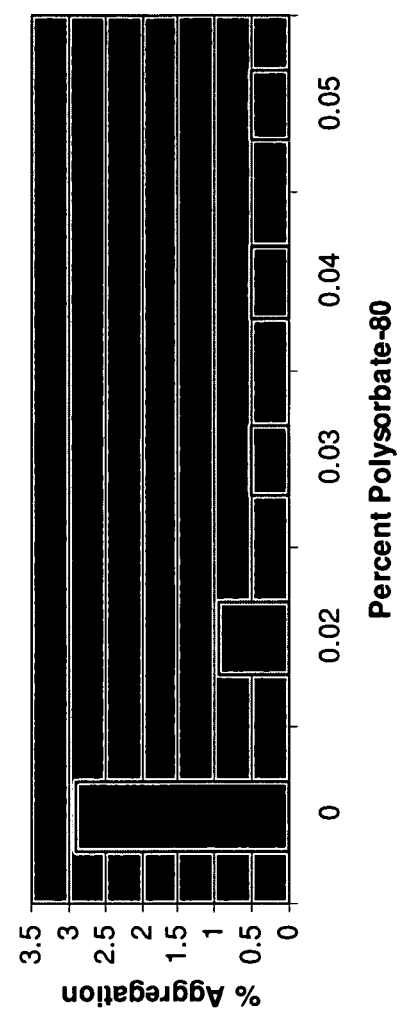
FIG. 3 shows the relationship between aggregation and various levels of polysorbate 80 for natalizumab (150 mg/mL) in the HOL formulation (HOL=20 mM histidine, 240 mM glycerol, pH 6; polysorbate 80 is a variable of the experiment).

The effect of polysorbate-80 levels on the stability of natalizumab during agitation are shown in FIG. 3, which shows data for natalizumab at 135-165 mg/mL. The minimum polysorbate-80 level for stability during agitation experiments is approximately 0.03% (w/v) for 150 mg/mL natalizumab, and 0.02% (w/v) for 20 mg/mL natalizumab. Thus the preferred polysorbate-80 concentration varies according to the antibody concentration.

Example 4

Long Term Storage of Natalizumab at Different Temperatures

The stability of 150 mg/mL natalizumab in various formulations and at between 2-8° C. and at 40° C. was assessed by measuring the percentage of aggregation using size exclusion chromatography as described in Example 2 above. Natalizumab (150 mg/mL) was either in HCN, HOL, PCN, or PST buffers as described in Example 2 above. Data for natalizumab stored at 40° C. was collected over five months; natalizumab stored at between 2-8° C. was collected over twenty-four months.

Figure 4:
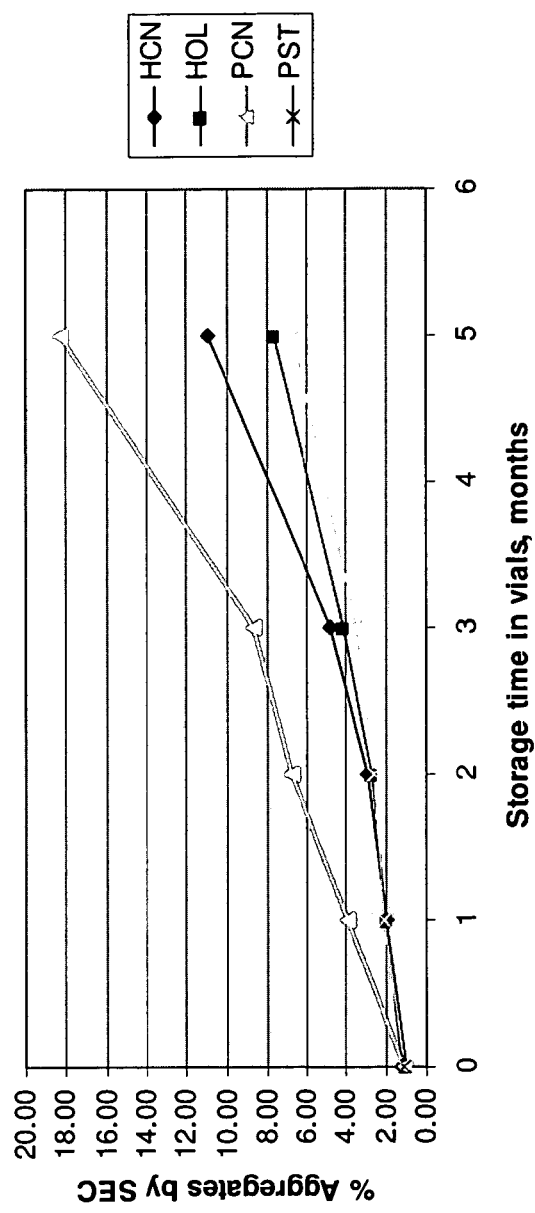
FIG. 4 shows percentage aggregation over time for natalizumab (150 mg/mL) stored at 40° C. in various formulations as described in FIG. 1.
Figure 5:
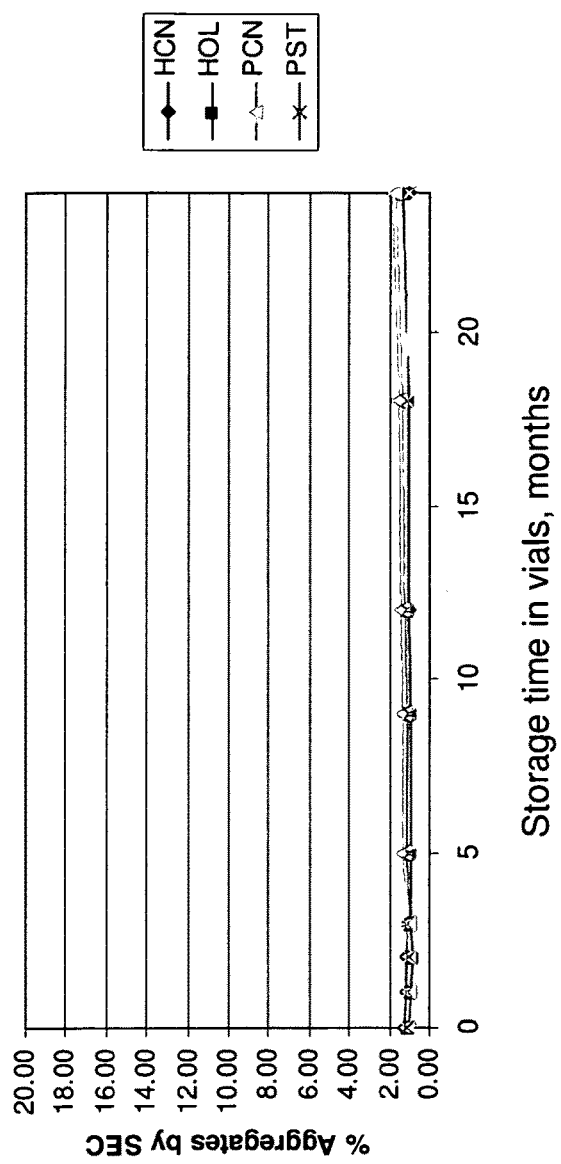
FIG. 5 shows percentage aggregation over time for natalizumab (150 mg/mL) stored in vials between 2-8° C. in various formulations as described in FIG. 1.

The results of the stability effects of various formulations of natalizumab (150 mg/mL) for storage at 40° C. are shown in FIG. 4; results for 2-8° C. storage are shown in FIG. 5. At a concentration of 150 mg/mL, natalizumab in the PST formulation (20 mM phosphate, 140 mM NaCl, 0.02% (w/v) polysorbate 80, pH 6) aggregated the least at 40° C. No significant differences in aggregation were observed when the antibody was stored at 2-8° C. for twenty-four months. These data demonstrated that the high-concentration of natalizumab in the PST formulation is particularly stable.

Example 5

Methionine Oxidation of Natalizumab Reduced in Phosphate Formulations

Figure 6:
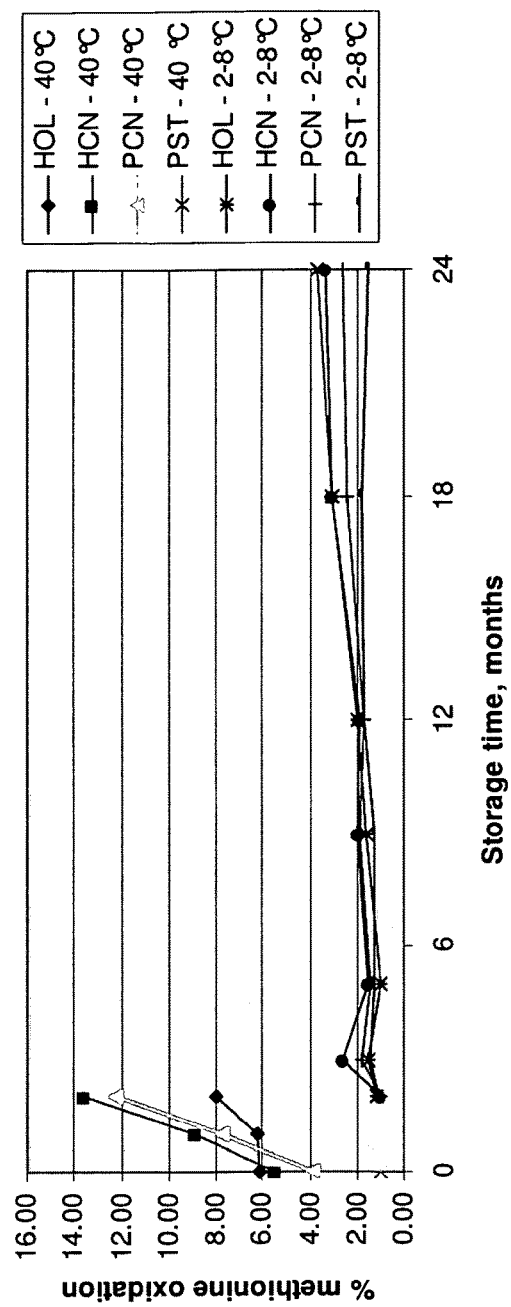
FIG. 6 shows percentage of methionine oxidation over time for natalizumab (150 mg/mL) stored between 2-8° C. and at 40° C. in various formulations as described in FIG. 1.

The tendency of methionine residues to oxidize in various formulations of natalizumab (150 mg/ml), and the protective effects of free methionine (10 mM) was studied by UV-HPLC characterization of endoLysC peptide maps. Natalizumab (150 mg/mL) was stored at between 2-8° C. and at 40° C. for up to twenty-four months in the histidine and phosphate formulations (HOL, HCN, PST, and PCN, as described in Example 2). The results, expressed as percentage of oxidized methionines, are shown in FIG. 6. For the phosphate formulations, oxidation of methionines in natalizumab at 150 mg/mL was significantly reduced and occurred at a lower rate in both temperature ranges, as compared to the histidine formulations.

Figure 7:
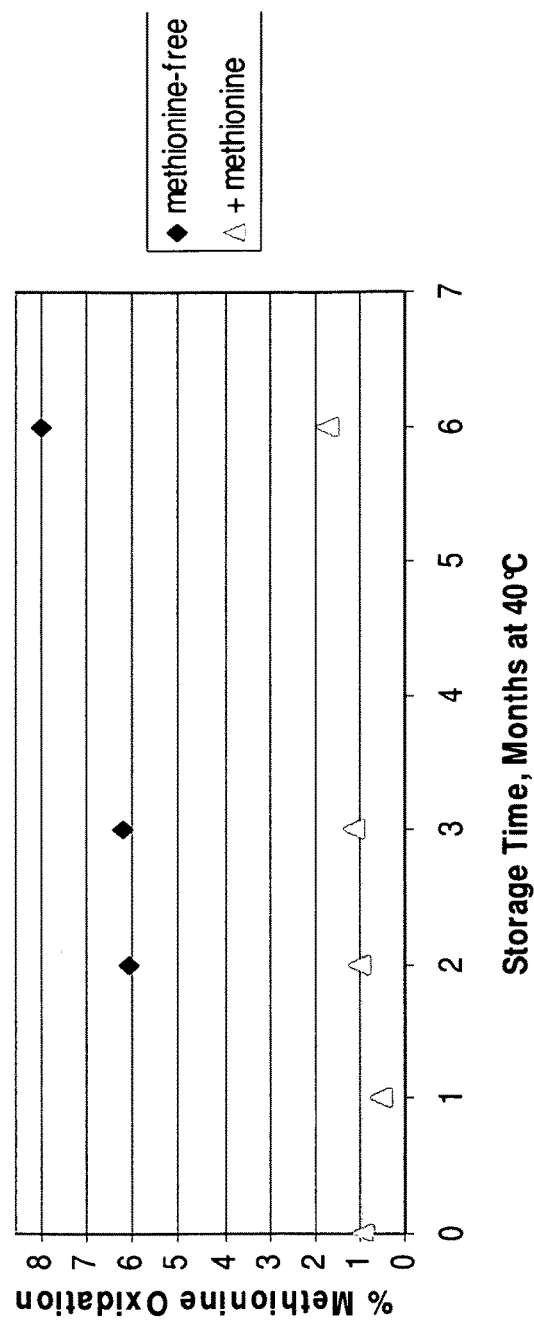
FIG. 7 shows percentage of methionine oxidation as a function of free scavenger excipient for natalizumab (150 mg/mL) over 6 months.

The anti-oxidant effects of excess free methionine (L-met) in the histidine formulations, such as HOL, were seen when compared to methionine-free formulations for natalizumab (150 mg/mL) stored at 40° C. over a time period of six months (FIG. 7). Percentage of methionine oxidation was quantitated as described above. Thus, formulating natalizumab at 150 mg/mL in phosphate buffers was more protective against methionine oxidation, and reduced the number of excipients required for stability at 150 mg/mL.

Example 6

Fragmentation Rate Greater in Histidine Buffers than in Phosphate Buffers

The rate of fragmentation of natalizumab (20 mg/mL, 50 mg/mL, 75 mg/mL, and 150 mg/mL) in various formulations (HOL: 20 mM histidine, 240 mM glycerol, 0.04% (w/v) polysorbate 80, pH 6, and PST: 20 mM phosphate, 140 mM NaCl, 0.02% (w/v) polysorbate 80, pH 6) was compared over time for 8 weeks. Fragmentation was quantified by measuring the percentage of half-antibody by non-reducing GelChip capillary electrophoresis.

Figure 8:
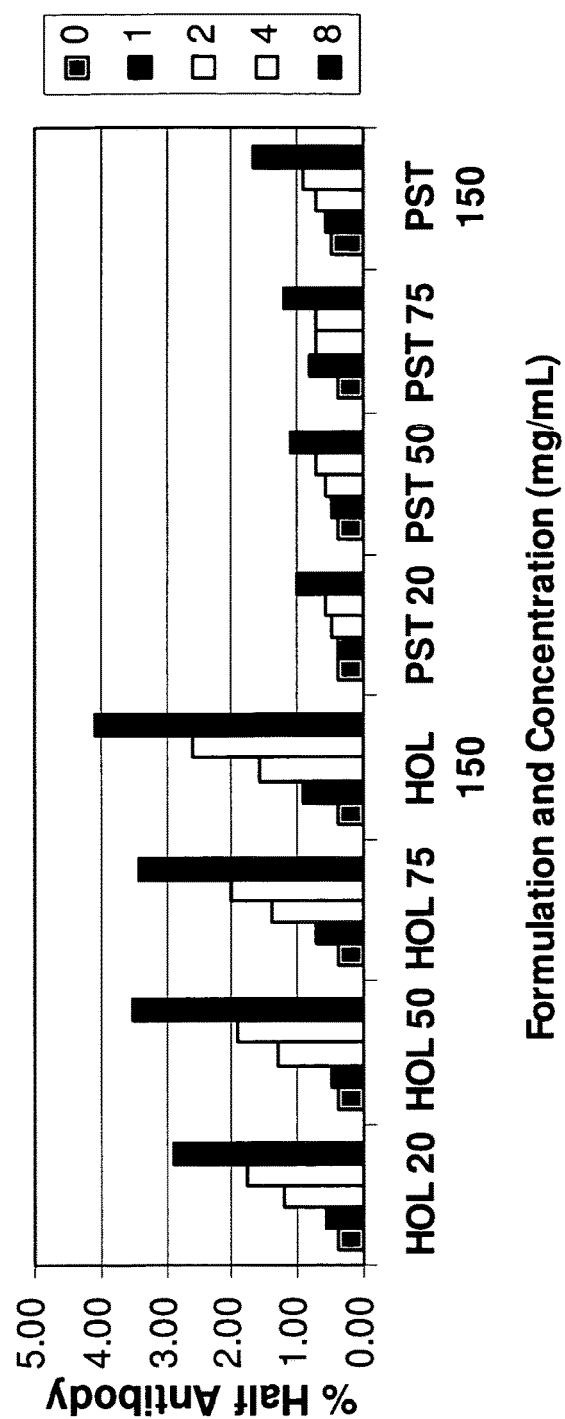
FIG. 8 shows fragmentation rates for natalizumab at various concentrations and in various formulations versus time (8 weeks).

The results of fragmentation studies, which measured the percentage of half antibodies over time for natalizumab at four different concentrations (20 mg/mL, 50 mg/mL, 75 mg/mL, and 150 mg/mL) and in two different formulations (HOL: 20 mM histidine, 240 mM glycerol, 0.04% (w/v) polysorbate 80, pH 6; and PST: 20 mM phosphate, 140 mM NaCl, 0.02% (w/v) polysorbate 80, pH 6) are shown in FIG. 8. The hinge cleavage rate is lower in phosphate than in histidine formulations. The histidine formulation environment is more reducing than the phosphate formulation environment (based on redox potential).

Example 7

Exemplary Formulations of Natalizumab Suitable for Subcutaneous or Intramuscular Administration In view of the experiments above, phosphate-based formulations were determined to be optimal for highly concentrated natalizumab compositions suitable for SC or IM administration. The compositions can also be diluted and used for IV administration. The above experiments indicate that natalizumab is less susceptible to oxidation when stored in phosphate formulations, such as PST and PCN, than when stored in the histidine formulations HOL and HCN. Therefore free methionine is typically not required in the phosphate formulations to prevent oxidation of natalizumab (see Example 5). The rate of fragmentation of natalizumab in the phosphate formulation PST was also observed to be less than that in the histidine formulation HOL (see Example 6). Long term stability was better in the phosphate formulations PST and PCN than in the histidine formulations HOL and HCN.

In some embodiments, each of the components of the formulations provided below can vary by 10%.

Example 8

Exemplary Formulation 150 mg/mL Natalizumab
10 mM sodium phosphate buffer
140 mM sodium chloride
0.04% (w/v) polysorbate 80 pH adjusted to pH 6.0±0.5

Example 9

Exemplary Formulation 150 mg/mL Natalizumab
10 mM sodium phosphate buffer
275 mM glycerol
0.04% (w/v) polysorbate 80
pH adjusted to pH 6.0±0.5

Example 10

Exemplary Formulation 150 mg/mL Natalizumab
10 mM sodium phosphate buffer
160 mM L-arginine hydrochloride
0.04% (w/v) polysorbate 80
pH adjusted to pH 6.0±0.5

Example 11

Exemplary Formulation 150 mg/mL Natalizumab
10 mM sodium phosphate buffer
9% (w/v) sucrose
0.04% (w/v) polysorbate 80
pH adjusted to pH 6.0±0.5

Example 12

Exemplary Formulation 150 mg/mL Natalizumab
10 mM sodium phosphate buffer
9% (w/v) sorbitol
0.04% (w/v) polysorbate 80
pH adjusted to pH 6.0±0.5

Example 13

Exemplary Formulation 150 mg/mL Natalizumab
20 mM L-histidine
240 mM glycerol
10 mM L-methionine
0.04% (w/v) polysorbate 80
pH adjusted to pH 6.0±0.5

Example 14

Exemplary Formulation 150 mg/mL Natalizumab
20 mM L-histidine
240 mM glycerol
0.04% (w/v) polysorbate 80
pH adjusted to pH 6.0±0.5

Example 15

Stability Data

The formulation provided above as example 8 was stored in a staked needle syringe, and stability data were measured at various time points. These data are summarized in the Tables below and indicate that the formulation, when stored in a syringe at 5° C., is stable for at least 18 to 24 months.

Formulation
150 mg/mL Natalizumab
10 mM sodium phosphate buffer
140 mM sodium chloride
0.04% (w/v) polysorbate 80
pH adjusted to pH 6.0±0.5

Aggregates:

| Time, months | % aggregates during storage at 5° C. |
|---|---|
| 0 | 0.7 |
| 1 | 0.7 |
| 2 | 0.7 |
| 3 | 0.7 |
| 6 | 0.8 |
| 8 | 0.9 |
| 12 | 1.0 |
| 18 | 1.1 |

Potency:

| Time, months | Relative Potency at 25° C. |
|---|---|
| 0 | 100 |
| 8 | 101 |
| 12 | 97 |

Lower pI isoforms:

| Time, months | % lower pI isoforms during storage at 5° C. |
|---|---|
| 0 | 15.2 |
| 1 | 15.4 |
| 2 | 15.1 |
| 3 | 15.6 |
| 6 | 13.5 |
| 8 | 13.3 |
| 12 | 15.0 |

Purity (% heavy+light chains):

| Time, months | % H + L during storage at 5° C. |
|---|---|
| 0 | 100 |
| 1 | 100 |
| 2 | 100 |
| 3 | 100 |
| 8 | 98.8 |
| 12 | 100 |

A number of embodiments of the invention have been described. Nevertheless, it will be understood that various modifications may be made without departing from the spirit and scope of the invention. Accordingly, other embodiments are within the scope of the following claims.

What is claimed is:

1. A method of treatment of a patient with an inflammatory disorder, the method comprising subcutaneously or intramuscularly administering a dose of 0.25 to 1.5 mL of a stable aqueous composition comprising 150 mg/mL natalizumab, 10 mM sodium phosphate buffer, 140 mM sodium chloride, and 0.04% (w/v) polysorbate 80, at pH 5.5-6.5.

2. The method of claim 1, wherein the composition has a viscosity of 5-30 cP at ambient temperature.

3. The method of claim 1, wherein the composition is stable for at least 12 months at a temperature of about 2° C. to about 8° C.

4. The method of claim 1, wherein the composition is stable for at least 24 months at a temperature of about 2° C. to about 8° C.

5. The method of claim 1, wherein the composition shows less than 10% aggregation following storage for at least 12 months at a temperature of about 2° C. to about 8° C.

6. The method of claim 1, wherein the composition shows less than 10% aggregation following storage for 18 months at a temperature of about 2° C. to about 8° C.

7. The method of claim 1, wherein the method comprises administering 1 mL of the composition.

8. The method of claim 1, wherein the inflammatory disorder is multiple sclerosis.

9. The method of claim 1, wherein the composition is administered subcutaneously.

10. The method of claim 1, wherein the composition comprises sodium phosphate monobasic, monohydrate or sodium phosphate dibasic heptahydrate or both.

11. The method of claim 1, wherein the composition retains its biological activity after storage of the composition for at least 12 months at a temperature of about 2° C. to about 8° C.

12. The method of claim 1, wherein the composition has a potency of at least 97% at 25° C. after storage for 12 months at a temperature of 5° C.

13. The method of claim 1, wherein the inflammatory disorder is asthma.

14. The method of claim 1, wherein the inflammatory disorder is an arthritic disorder.

15. The method of claim 1, wherein the inflammatory disorder is diabetes.

16. The method of claim 1, wherein the inflammatory disorder is a fibrotic disorder.

17. The method of claim 1, wherein the inflammatory disorder is an inflammatory bowel disease.

18. The method of claim 1, wherein the method comprises subcutaneously or intramuscularly administering two doses of 1 mL of the composition.

19. A method of treatment of a patient with an inflammatory disorder, the method comprising subcutaneously or intramuscularly administering a dose of 0.25 to 1.5 mL of a stable aqueous composition consisting essentially of 150 mg/mL natalizumab, 10 mM sodium phosphate buffer, 140 mM sodium chloride, and 0.04% (w/v) polysorbate 80, at pH 5.5-6.5.

20. The method of claim 19, wherein the composition has a viscosity of 5-30 cP at ambient temperature.

21. The method of claim 19, wherein the composition is stable for at least 12 months at a temperature of about 2° C. to about 8° C.

22. The method of claim 19, wherein the composition is stable for at least 24 months at a temperature of about 2° C. to about 8° C.

23. The method of claim 19, wherein the composition shows less than 10% aggregation following storage for at least 12 months at a temperature of about 2° C. to about 8° C.

24. The method of claim 19, wherein the composition shows less than 10% aggregation following storage for 18 months at a temperature of about 2° C. to about 8° C.

25. The method of claim 19, wherein the method comprises administering 1 mL of the composition.

26. The method of claim 19, wherein the inflammatory disorder is multiple sclerosis.

27. The method of claim 19, wherein the composition retains its biological activity after storage of the composition for at least 12 months at a temperature of about 2° C. to about 8° C.

28. The method of claim 19, wherein the composition has a potency of at least 97% at 25° C. after storage for 12 months at a temperature of 5° C.

29. The method of claim 19, wherein the inflammatory disorder is an inflammatory bowel disease.

30. The method of claim 19, wherein the method comprises subcutaneously or intramuscularly administering two doses of 1 mL of the composition.

31. A method of treatment of a patient with an inflammatory disorder, the method comprising subcutaneously or intramuscularly administering a dose of 0.25 to 1.5 mL of a stable aqueous composition consisting of 150 mg/mL natalizumab, 10 mM sodium phosphate buffer, 140 mM sodium chloride, and 0.04% (w/v) polysorbate 80, at pH 5.5-6.5.

32. The method of claim 31, wherein the composition has a viscosity of 5-30 cP at ambient temperature.

33. The method of claim 31, wherein the composition is stable for at least 12 months at a temperature of about 2° C. to about 8° C.

34. The method of claim 31, wherein the composition is stable for at least 24 months at a temperature of about 2° C. to about 8° C.

35. The method of claim 31, wherein the composition shows less than 10% aggregation following storage for at least 12 months at a temperature of about 2° C. to about 8° C.

36. The method of claim 31, wherein the composition shows less than 10% aggregation following storage for 18 months at a temperature of about 2° C. to about 8° C.

37. The method of claim 31, wherein the method comprises administering 1 mL of the composition.

38. The method of claim 31, wherein the inflammatory disorder is multiple sclerosis.

39. The method of claim 31, wherein the composition retains its biological activity after storage of the composition for at least 12 months at a temperature of about 2° C. to about 8° C.

40. The method of claim 31, wherein the composition has a potency of at least 97% at 25° C. after storage for 12 months at a temperature of 5° C.

41. The method of claim 31, wherein the inflammatory disorder is an inflammatory bowel disease.

42. The method of claim 31, wherein the method comprises subcutaneously or intramuscularly administering two doses of 1 mL of the composition.

43. A method of treatment of a patient with multiple sclerosis, the method comprising subcutaneously or intramuscularly administering a dose of 0.25 to 1.5 mL of an aqueous composition comprising 150 mg/mL natalizumab, 10 mM sodium phosphate buffer, 140 mM sodium chloride, and 0.04% (w/v) polysorbate 80, at pH 5.5-6.5, wherein the composition has a viscosity of 5-30 cP at ambient temperature and shows less than 10% aggregation after storage for at least 12 months at a temperature of about 2° C. to about 8° C.

44. The method of claim 43, wherein the method comprises subcutaneously or intramuscularly administering two doses of 1 mL of the composition.

\* \* \* \* \*